United States Patent
Kawabori et al.

(10) Patent No.: US 12,290,335 B2
(45) Date of Patent: May 6, 2025

(54) METHOD, PROGRAM, AND DEVICE FOR EVALUATING STATE OF MOTOR FUNCTION

(71) Applicant: RAINBOW INC., Hokkaido (JP)

(72) Inventors: Masahito Kawabori, Hokkaido (JP); Khin Khin Tha, Hokkaido (JP)

(73) Assignee: RAINBOW INC., Hokkaido (JP)

(*) Notice: Subject to any disclaimer, the term of this patent is extended or adjusted under 35 U.S.C. 154(b) by 513 days.

(21) Appl. No.: 17/763,280

(22) PCT Filed: Sep. 29, 2020

(86) PCT No.: PCT/JP2020/036854
§ 371 (c)(1),
(2) Date: Mar. 24, 2022

(87) PCT Pub. No.: WO2021/065894
PCT Pub. Date: Apr. 8, 2021

(65) Prior Publication Data
US 2022/0346649 A1  Nov. 3, 2022

(30) Foreign Application Priority Data

Sep. 30, 2019 (JP) .................... 2019-181051

(51) Int. Cl.
*A61B 5/00* (2006.01)
*A61B 5/055* (2006.01)
*G01R 33/563* (2006.01)

(52) U.S. Cl.
CPC ............ *A61B 5/0042* (2013.01); *A61B 5/055* (2013.01); *A61B 5/4848* (2013.01); *G01R 33/56341* (2013.01)

(58) Field of Classification Search
CPC ...... A61B 5/0042; A61B 5/055; A61B 5/4848
See application file for complete search history.

(56) References Cited

U.S. PATENT DOCUMENTS

2008/0122440 A1   5/2008  Sakai
2008/0205733 A1*  8/2008  Laidlaw ............... G16H 50/50
                                            382/131

(Continued)

FOREIGN PATENT DOCUMENTS

| JP | 2006508707 A | 3/2006 |
|----|---|---|
| JP | 2008510560 A | 4/2008 |
| JP | 2008-132032 A | 6/2008 |
| JP | 2011-139799 A | 7/2011 |
| JP | 2011143105 A | 7/2011 |
| JP | 2015534844 A | 12/2015 |

(Continued)

OTHER PUBLICATIONS

Mastropietro Alfonso et al: "Microstructural characterization of corticospinal tract in subacute and chronic stroke patients with distal lesions by means of advanced diffusion MRI", Neuroradiology, Springer Berlin Heidelberg, Berlin/Heidelberg, vol. 61, No. 9, Jul. 1, 2019 (Jul. 1, 2019), pp. 1033-1045, XP036857179, ISSN: 0028-3940, Doi: 10.1007/S00234-019-02249-2 [retrieved on Jul. 1, 2019].

(Continued)

*Primary Examiner* — Joel F Brutus
(74) *Attorney, Agent, or Firm* — Renner, Otto, Boisselle & Sklar, LLP

(57) ABSTRACT

The present disclosure relates to: a method for evaluating a state of a motor function of a patient who has or is suspected of having brain damage by using parameters obtained from a diffusion weighted image of the patient's brain; a program for executing the method in a computer; and an image processing device and an MRI device which can be used in practicing the method. According to the present disclosure, the motor function state of a patient who has or is suspected of having brain damage can be evaluated, and it is also possible to predict the recovery of the motor function after regeneration treatment. Accordingly, whether the patient is suitable for the regeneration treatment can be determined before the start of the treatment.

16 Claims, 15 Drawing Sheets

(56) References Cited

U.S. PATENT DOCUMENTS

| | | | |
|---|---|---|---|
| 2011/0066407 A1* | 3/2011 | Butson | A61B 5/7257 |
| | | | 703/2 |
| 2015/0379713 A1 | 12/2015 | Puybasset et al. | |
| 2017/0285124 A1* | 10/2017 | Verma | G01R 33/5608 |
| 2018/0168499 A1 | 6/2018 | Bergold | |
| 2018/0206800 A1* | 7/2018 | Jasperse | G06T 7/0014 |
| 2018/0263569 A1 | 9/2018 | Wang et al. | |

FOREIGN PATENT DOCUMENTS

| | | |
|---|---|---|
| WO | 2004022156 A2 | 3/2004 |
| WO | 2006021952 A2 | 3/2006 |

OTHER PUBLICATIONS

Maraka Stefania et al: "Degree of corticospinal tract damage correlates with motor function after stroke", Annals of Clinical and Translational Neurology, Oct. 31, 2014 (Oct. 31, 2014), pp. 891-899, XP093081585, GB ISSN: 2328-9503, DOI: 10.1002/acn3.132 Retrieved from the Internet: URL:https://onlinelibrary.wiley.com/doi/full-XML/10.1002/acn3.132 [retrieved on Sep. 13, 2023].

Sotak Christopher H.: "The role of diffusion tensor imaging in the evaluation of ischemic brain injury—a review", NMR in Biomedicine. , vol. 15, No. 7-8, Nov. 1, 2002 (Nov. 1, 2002), pp. 561-569, XP93081571, GBISSN: 0952-3480, DOI: 10.1002/nbm.786.

European Extended Search Report for corresponding European Application No. 20871340.4 dated Sep. 22, 2023.

International Search Report for related International Application No. PCT/JP2020/036854 mailed Dec. 22, 2020 and its English Translation.

Stem Cell Therapies as an Emerging Paradigm in Stroke Participants, Stroke 40(2):510-5. 2009.

Notice of Reasons for Refusal for corresponding Japanese Patent Application No. 2021-169636, issued Jan. 7, 2025, with English translation.

* cited by examiner

METHOD, PROGRAM, AND DEVICE FOR EVALUATING STATE OF MOTOR FUNCTION

This application is a national phase of International Application No. PCT/JP2020/036854 filed 29 Sep. 2020, which claims priority to Japan Application No. 2019-181051 filed 30 Sep. 2019, the entireties of which are hereby incorporated by reference.

TECHNICAL FIELD

The present disclosure relates to a method for evaluating a state of a motor function of a patient who has or is suspected of having a brain injury, and a program, an image analysis apparatus, and an MRI apparatus that can be used in the implementation of the method. In particular, the present disclosure relates to a method for predicting motor function recovery after regeneration therapy of a patient having a brain focal injury.

BACKGROUND ART

In recent years, regeneration medical treatment has drawn attention as a new therapeutic method for central nervous diseases (such as cerebral infarction, cerebral hemorrhage, head trauma, or Parkinson's disease), and development of a plurality of cell medicaments is being advanced. In particular, it is considered that therapy with direct transplantation for directly delivering a cell into the brain can deliver more cells into the brain because said therapy can avoid blocking by the blood-brain barrier.

In cell therapy, it is important to determine which patient is suitable for cell therapy prior to start of the therapy because the recovery degree of a patient actually administered with a cell varies (Non Patent Literature 1).

CITATION LIST

Non Patent Literature

[NPL 1] Stem Cell Therapies as an Emerging Paradigm in Stroke Participants, Stroke 40 (2): 510-5. 2009

DISCLOSURE OF INVENTION

Solution to Problem

The present disclosure provides a means for evaluating a state of a motor function of a patient who has or is suspected of having a brain injury such as a brain focal injury. The present disclosure particularly provides a means for determining whether such a patient is suitable for regeneration therapy, in other words, whether regeneration therapy can be expected to be effective for said patient, prior to start of the therapy.

The present inventors found that a state of a motor function of a patient having a brain focal injury is correlated with a parameter obtained from a diffusion weighted image of the brain of the patient.

Thus, the present disclosure provides the following items.
(Item 1)
A method for evaluating a state of a motor function of a patient who has or is suspected of having a brain injury, the method comprising:
  obtaining a physiological indicator value with an outer surface region on the side of an injured hemisphere of a brain of the patient as a region of interest; and
  performing computation to calculate a value indicating the state of the motor function of the patient by comparing the physiological indicator value with a reference physiological indicator value.
(Item 2)
The method of item 1, wherein the physiological indicator value is obtained from a diffusion weighted image of the brain of the patient which is obtained by diffusion tensor imaging (DTI) method or diffusion kurtosis imaging (DKI) method.
(Item 3)
The method of any one of the preceding items, wherein the physiological indicator value includes an FA (fractional anisotropy) value.
(Item 4)
The method of any one of the preceding items, wherein the region of interest is set to a precentral gyrus of the brain.
(Item 5)
The method of any one of the preceding items, wherein the state of the motor function is a state of a motor function after regeneration therapy.
(Item 6)
The method of any one of the preceding items, wherein the reference physiological indicator value is obtained with an outer surface region on the side of an uninjured hemisphere of the brain of the patient as a region of interest.
(Item 7)
The method of any one of the preceding items, wherein the performing computation calculates a value represented by the physiological indicator value/the reference physiological indicator value.
(Item 8)
The method of any one of the preceding items, wherein the performing computation evaluates the state of the motor function of the patient by substituting the calculated value indicating the state of the motor function of the patient in a regression line which is prepared in advance and has a value indicating a state of a motor function of a patient and a motor function recovery degree as variables.
(Item 9)
The method of any one of the preceding items, wherein the performing computation calculates a level of a likelihood that the patient reaches a desired motor function recovery degree after regeneration therapy by comparing the calculated value indicating the state of the motor function of the patient with a reference value which is prepared in advance.
(Item 10)
A computer program for causing a computer to execute processing of a method for evaluating a state of a motor function of a brain of a patient who has or is suspected of having a brain injury, wherein the method comprises the following processes:
  causing the computer to obtain a physiological indicator value with an outer surface region on the side of an injured hemisphere of the brain of the patient as a region of interest; and
  causing the computer to perform computation to calculate a value indicating the state of the motor function of the patient by comparing the physiological indicator value with a reference physiological indicator value.
(Item 11)
A storage medium for storing a computer program for causing a computer to execute processing of a method for evaluating a state of a motor function of a brain of a patient who has or is suspected of having a brain injury, wherein the method comprises the following processes:

causing the computer to obtain a physiological indicator value with an outer surface region on the side of an injured hemisphere of the brain of the patient as a region of interest; and causing the computer to perform computation to calculate a value indicating the state of the motor function of the patient by comparing the physiological indicator value with a reference physiological indicator value.

(Item 12)

A system for evaluating a state of a motor function of a brain of a patient who has or is suspected of having a brain injury, the system comprising:

a means for obtaining a physiological indicator value with an outer surface region on the side of an injured hemisphere of the brain of the patient as a region of interest; and a means for performing computation to calculate a value indicating the state of the motor function of the patient by comparing the physiological indicator value with a reference physiological indicator value.

(Item 13)

An image analysis apparatus comprising:

a region of interest setting unit that sets an outer surface region on the side of an injured hemisphere as a first region of interest and sets an outer surface region on the side of an uninjured hemisphere as a second region of interest in a diffusion weighted image of a brain of a patient who has or is suspected of having a brain injury;

a physiological indicator value calculating unit that calculates an injured hemisphere-side physiological indicator value and an uninjured hemisphere-side physiological indicator value in the first region of interest and the second region of interest, respectively; and a computing unit that performs computation to calculate a value indicating a state of a motor function of the patient by comparing the injured hemisphere-side physiological indicator value and the uninjured hemisphere-side physiological indicator value.

(Item 14)

An MRI apparatus comprising:

a nuclear magnetic resonance imaging unit that images a brain of a patient who has or is suspected of having a brain injury;

an image generating unit that generates a diffusion weighted image from echo data that the nuclear magnetic resonance imaging unit acquires;

a region of interest setting unit that sets an outer surface region on the side of an injured hemisphere as a first region of interest and sets an outer surface region on the side of an uninjured hemisphere as a second region of interest in the diffusion weighted image;

a physiological indicator value calculating unit that calculates an injured hemisphere-side physiological indicator value and an uninjured hemisphere-side physiological indicator value in the first region of interest and the second region of interest, respectively; and a computing unit that performs computation to calculate a value indicating a state of a motor function of the patient by comparing the injured hemisphere-side physiological indicator value and the uninjured hemisphere-side physiological indicator value.

The present disclosure also provides the following.

(1) A method for predicting motor function recovery after regeneration therapy of a patient having a brain focal injury, the method comprising:

setting a precentral gyrus on the side of an injured hemisphere as a first region of interest and setting a precentral gyrus on the side of an uninjured hemisphere as a second region of interest in a diffusion tensor image of a brain of the patient;

calculating an injured hemisphere-side FA and an uninjured hemisphere-side FA that are a fractional anisotropy in the first region of interest and the second region of interest, respectively;

calculating an rFA represented by the injured hemisphere-side FA/the uninjured hemisphere-side FA; and performing computation to predict the motor function recovery of the patient after regeneration therapy based on the calculated rFA.

(2) The method of (1), wherein the performing computation is the calculating a predicted value of a motor function recovery degree after regeneration therapy of the patient by substituting the calculated rFA in a regression line which is prepared in advance and has an rFA and a motor function recovery degree as variables.

(3) The method of (1), wherein the performing computation is the calculating a level of a likelihood that the patient reaches a desired motor function recovery degree after regeneration therapy by comparing the calculated rFA with a reference rFA which is prepared in advance.

(4) A program for predicting motor function recovery after regeneration therapy of a patient having a brain focal injury for causing a computer to execute:

processing of setting a precentral gyrus on the side of an injured hemisphere as a first region of interest and setting a precentral gyrus on the side of an uninjured hemisphere as a second region of interest in a diffusion tensor image of a brain of the patient;

processing of calculating an injured hemisphere-side FA and an uninjured hemisphere-side FA that are a fractional anisotropy in the first region of interest and the second region of interest, respectively;

processing of calculating an rFA represented by the injured hemisphere-side FA/the uninjured hemisphere-side FA; and processing of performing computation to predict the motor function recovery of the patient after regeneration therapy based on the calculated rFA.

(5) The program of (4), wherein the processing of performing computation is processing of calculating a predicted value of a motor function recovery degree after regeneration therapy of the patient by substituting the calculated rFA in a regression line which is prepared in advance and has an rFA and a motor function recovery degree as variables.

(6) The program of (4), wherein the processing of performing computation is processing of calculating a level of a likelihood that the patient reaches a desired motor function recovery degree after regeneration therapy by comparing the calculated rFA with a reference rFA which is prepared in advance.

(7) A computer readable storage medium with the program of any one of (4) to (6) stored thereon.

(8) An image analysis apparatus comprising:

a region of interest setting unit that sets a precentral gyrus on the side of an injured hemisphere as a first region of interest and sets a precentral gyrus on the side of an uninjured hemisphere as a second region of interest in a diffusion tensor image of a brain of a patient having a brain focal injury;

an FA calculating unit that calculates an injured hemisphere-side FA and an uninjured hemisphere-side FA that are a fractional anisotropy in the first region of interest and the second region of interest, respectively;

an rFA calculating unit that calculates an rFA represented by the injured hemisphere-side FA/the uninjured hemisphere-side FA; and a recovery prediction computing unit that performs computation to predict motor function recovery of the patient after regeneration therapy based on the calculated rFA.

(9) An MRI apparatus comprising:

a nuclear magnetic resonance imaging unit that images a brain of a patient having a brain focal injury;

an image generating unit that generates a diffusion tensor image from echo data that the nuclear magnetic resonance imaging unit acquires;

a region of interest setting unit that sets a precentral gyrus on the side of an injured hemisphere as a first region of interest and sets a precentral gyrus on the side of an uninjured hemisphere as a second region of interest in the diffusion tensor image;

an FA calculating unit that calculates an injured hemisphere-side FA and an uninjured hemisphere-side FA that are a fractional anisotropy in the first region of interest and the second region of interest, respectively;

an rFA calculating unit that calculates an rFA represented by the injured hemisphere-side FA/the uninjured hemisphere-side FA; and a recovery prediction computing unit that performs computation to predict motor function recovery of the patient after regeneration therapy based on the calculated rFA.

The present disclosure is intended so that one or more of the above features can be provided not only as the explicitly disclosed combinations, but also as other combinations thereof. Additional embodiments and advantages of the present disclosure are recognized by those skilled in the art by reading and understanding the following detailed explanation as needed.

The features and significant action/effect of the present disclosure other than those described above will be clear to those skilled in the art by referring to the following section of the embodiments and the drawings of the invention.

Advantageous Effects

According to the present disclosure, it is possible to evaluate a state of a motor function of a patient who has or is suspected of having a brain injury such as a brain focal injury, it is thereby possible to predict motor function recovery after regeneration therapy of the patient, and it is also possible to determine whether the patient is suitable for regeneration therapy prior to start of the therapy.

DESCRIPTION OF EMBODIMENTS

Figure 1:
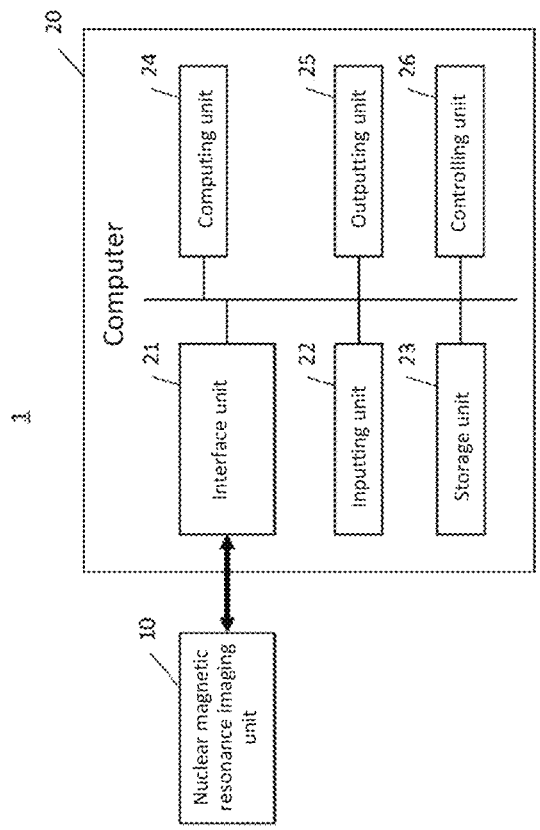
FIG. 1 is a block diagram showing the overall configuration of an MRI apparatus that is one embodiment of the present disclosure.

The present disclosure is explained hereinafter while showing the best mode. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

The definition and/or the basic technical contents of the terms particularly used herein are appropriately explained hereinafter.

As used herein, "about" means±10% of the numerical value that follows.

As used herein, "outer surface region" refers to the region on the outer side of the cerebrum, and particularly refers to the gyrus. For example, the outer surface region includes fornicate gyrus, superior frontal gyrus, middle frontal gyrus, inferior frontal gyrus, superior temporal gyrus, middle temporal gyrus, inferior temporal gyrus, fusiform gyrus, parahippocampal gyrus, transverse temporal gyrus, precentral gyrus, postcentral gyrus, supramarginal gyrus, angular gyrus, cingulate gyrus, dentate gyrus, paracentral lobule, cuneus, precuneus, lingual gyrus, and the like.

As used herein, "physiological indicator value" refers to an indicator value that is obtained from a diffusion weighted image of the brain of diffusion tensor imaging (DTI), diffusion kurtosis imaging (DKI), or the like, and includes MK (mean kurtosis), AK (axial kurtosis), RK (radial kurtosis), FA (fractional anisotropy), KFA (kurtosis fractional anisotropy), MD (mean diffusivity), AD (axial diffusivity), and RD (radial diffusivity).

As used herein, "state of a motor function" refers to a state of a motor function that is comprehensively controlled by the function of the brain, and "evaluation of a state of a motor function" includes evaluating or predicting whether the motor function is normal or the motor function is partially or completely paralyzed or the like at the present time or after therapy from the state of the brain of a subject. For example, "evaluation of a state of a motor function" includes prediction or the like of recovery of the function of the brain controlling movement by regeneration therapy or the like.

PREFERRED EMBODIMENTS

Preferred embodiments of the present disclosure are explained hereinafter. The embodiments provided hereinafter are provided for better understanding of the present disclosure, wherein the scope of the present disclosure should not be limited to the description below. Therefore, it is clear that those skilled in the art can appropriately make modifications within the scope of the present disclosure while considering the description herein. In addition, the following embodiments of the present disclosure can be used alone or can be used in combination.

In one aspect of the present disclosure, a method for evaluating a state of a motor function of a patient who has or is suspected of having a brain injury, the method comprising: obtaining a physiological indicator value with an outer surface region on the side of an injured hemisphere of a brain of the patient as a region of interest; and performing computation to calculate a value indicating the state of the motor function of the patient by comparing the physiological indicator value with a reference physiological indicator value, is provided.

In one embodiment, a physiological indicator value can be obtained from an image of the brain of a patient obtained by diffusion tensor imaging (DTI) method or diffusion kurtosis imaging (DKI) method. With diffusion tensor imaging (DTI) method, a region of interest (ROI) created by tracing an anatomy is set and a physiological indicator value such as the FA value or MD value in the region of interest is measured, whereby the corticospinal tract can be tracked.

In general, ROI setting in diffusion tensor imaging (DTI) method is manually performed, but tracking of the corticospinal tract in this technique relies on the experience of the measurer. Thus, in one embodiment, DKI method can be used without relying on the measurer and as a quantitative image index. Although DTI method assumes that diffusion of water molecules is a normal distribution, it is known that diffusion of water molecules in a living body does not show a normal distribution. Thus, with a diffusion imaging method that does not assume a normal distribution as in DKI method, diffusion of water molecules in a living body can be more precisely reflected. Therefore, in one embodiment of the present disclosure, a diffusion image index capable of predicting the therapeutic effect of cell administration to a patient with cerebral infarction precisely and without relying on the experience of the measurer or the like can be obtained with DKI method.

In one embodiment, a physiological indicator value obtained from a diffusion weighted image of the brain of a patient obtained by diffusion tensor imaging (DTI) method or diffusion kurtosis imaging (DKI) method as described above is not particularly limited as long as the physiological indicator value is an index obtained by a diffusion weighted image that is formed image with the direction and the rate of diffusion of water molecules in tissue as parameters. For example, a diffusion index such as MK (mean kurtosis), AK (axial kurtosis), RK (radial kurtosis), FA (fractional anisotropy), KFA (kurtosis fractional anisotropy), MD (mean diffusivity), AD (axial diffusivity), and RD (radial diffusivity) can be used. In one embodiment, it is also possible to use these diffusion indexes alone or combine two or more thereof to be used.

In one embodiment of the present disclosure, the ROI in DTI and DKI may be set anywhere on the outer surface region of the brain and is not particularly limited. In one embodiment, the ROI is preferably set to the precentral gyrus.

In one embodiment of the present disclosure, a state of a motor function of a subject can be evaluated from a physiological indicator value obtained from an image of the brain of a patient obtained by diffusion tensor imaging (DTI) method or diffusion kurtosis imaging (DKI) method as described above, wherein this motor function may be a function at the present time or after therapy, and it is also possible to predict a recovery state of the motor function after regeneration therapy.

In one embodiment of the present disclosure, a state of a motor function can be evaluated by comparing a physiological indicator value obtained when the ROI is placed on the side of an injured hemisphere of the brain and a physiological indicator value obtained when the ROI is placed on the side of an uninjured hemisphere of the brain (called reference physiological indicator value), and preferably by calculating a value represented by the physiological indicator value/the reference physiological indicator value.

In one embodiment of the present disclosure, a state of a motor function also can be evaluated by substituting a value represented by a physiological indicator value/a reference physiological indicator value in a regression line which has a value indicating a state of a motor function of a patient and a motor function recovery degree as variables. In another embodiment, the possibility that a patient reaches a desired motor function recovery degree after regeneration therapy also comparing a value represented by a can be indicated by physiological indicator value/a reference physiological indicator value with a reference value indicating the likelihood that the patient reaches the desired motor function recovery degree after regeneration therapy.

In view of the foregoing, with the method of the present disclosure, it is possible to evaluate a state of a motor function of a subject and it is also possible to evaluate the state of the motor function after regeneration therapy, in other words, predict whether the function motor recovers by regeneration therapy, so that it is possible to determine which patient is suitable for cell therapy prior to start of the therapy, and it is also possible to select a patient for which the therapy is highly effective. The present disclosure also provides a computer program for causing a computer to execute the above-described method, a storage medium for storing said program, and a system for executing the above-described method.

Specifically, in one aspect of the present disclosure, a computer program for causing a computer to execute processing of a method for evaluating a state of a motor function of a brain of a patient who has or is suspected of having a brain injury, wherein the method comprises the following processes: causing the computer to obtain a physiological indicator value with an outer surface region on the side of an injured hemisphere of the brain of the patient as a region of interest; and causing the computer to perform computation to calculate a value indicating the state of the motor function of the patient by comparing the physiological indicator value with a reference physiological indicator value, is provided.

In another aspect of the present disclosure, a storage medium for storing a computer program for causing a computer to execute processing of a method for evaluating a state of a motor function of a brain of a patient who has or is suspected of having a brain injury, wherein the method comprises the following processes:

causing the computer to obtain a physiological indicator value with an outer surface region on the side of an injured hemisphere of the brain of the patient as a region of interest; and causing the computer to perform computation to calculate a value indicating the state of the motor function of the patient by comparing the physiological indicator value with a reference physiological indicator value, is provided.

In another aspect of the present disclosure, a system for evaluating a state of a motor function of a brain of a patient who has or is suspected of having a brain injury, the system comprising:

a means for obtaining a physiological indicator value with an outer surface region on the side of an injured hemisphere of the brain of the patient as a region of interest; and a means for performing computation to calculate a value indicating the state of the motor function of the patient by comparing the physiological indicator value with a reference physiological indicator value, is provided.

Further, in one aspect of the present disclosure, an image analysis apparatus and an MRI apparatus that can be used in the implementation of a method for evaluating a state of a motor function of a patient who has or is suspected of having a brain injury as described above can be provided.

Specifically, in one aspect of the present disclosure, an image analysis apparatus comprising:

a region of interest setting unit that sets an outer surface region on the side of an injured hemisphere as a first region of interest and sets an outer surface region on the side of an uninjured hemisphere as a second region of interest in a diffusion weighted image of a brain of a patient who has or is suspected of having a brain injury;

a physiological indicator value calculating unit that calculates an injured hemisphere-side physiological indicator value and an uninjured hemisphere-side physiological indicator value in the first region of interest and the second region of interest, respectively; and a computing unit that performs computation to calculate a value indicating a state of a motor function of the patient by comparing the injured hemisphere-side physiological indicator value and the uninjured hemisphere-side physiological indicator value is provided.

In another aspect of the present disclosure, an MRI apparatus comprising:

a nuclear magnetic resonance imaging unit that images a brain of a patient who has or is suspected of having a brain injury;

an image generating unit that generates a diffusion weighted image from echo data that the nuclear magnetic resonance imaging unit acquires;

a region of interest setting unit that sets an outer surface region on the side of an injured hemisphere as a first region of interest and sets an outer surface region on the side of an uninjured hemisphere as a second region of interest in the diffusion weighted image;

a physiological indicator value calculating unit that calculates an injured hemisphere-side physiological indicator value and an uninjured hemisphere-side physiological indicator value in the first region of interest and the second region of interest, respectively; and a computing unit that performs computation to calculate a value indicating a state of a motor function of the patient by comparing the injured hemisphere-side physiological indicator value and the uninjured hemisphere-side physiological indicator value is provided.

The detailed configuration of the image analysis apparatus and the MRI apparatus of the present disclosure can comprise the same configuration as that of the image analysis apparatus and the MRI apparatus described in detail in other portions of the present specification.

Another aspect of the present disclosure relates to a method for predicting motor function recovery after regeneration therapy of a patient having a brain focal injury, and a program, an image analysis apparatus, and an MRI apparatus that can be used in the implementation of the method.

An exemplary embodiment of a method for predicting motor function recovery after regeneration therapy of a patient having a brain focal injury and an MRI apparatus that can be used in the implementation of the method are explained while referring to FIGS. 1 to 5.

FIG. 1 shows a block diagram showing the overall configuration of an MRI apparatus that is one embodiment of the present disclosure. An MRI apparatus 1 has a nuclear magnetic resonance imaging unit 10 and a computer 20.

The nuclear magnetic resonance imaging unit 10 is an imaging unit that is used in any known MRI apparatus which can acquire echo data necessary for a DTI image. In one example, the nuclear magnetic resonance imaging unit 10 has: a bed; a magnet stand comprising a static magnetic field magnet, a gradient magnetic field coil, and an RF coil; and a sequence controlling unit. In the nuclear magnetic resonance imaging unit 10, the bed on which a patient is lying is inserted into an opening part of the magnet stand. The static magnetic field magnet of the magnet stand generates a static magnetic field, and the gradient magnetic field coil applies a gradient magnetic field accordingly. Next, an RF coil for transmission generates a high frequency magnetic field, and an RF coil for reception receives an echo signal emitted from the patient by generation of the high frequency magnetic field. The received echo signal is digitized and transmitted to the sequence controlling unit as echo data. The sequence controlling unit controls imaging based on sequence information transmitted from the computer 20, and also transfers the received echo data to the computer 20.

The computer 20 is an apparatus that controls the nuclear magnetic resonance imaging unit 10, collects data, reconstructs an image, and analyzes an image, and has an interface unit 21, an inputting unit 22, a storage unit 23, a computing unit 24, an outputting unit 25, and a controlling unit 26.

The interface unit 21 controls an input and an output of various data such as echo data that is exchanged with the sequence controlling unit of the nuclear magnetic resonance imaging unit 10. The interface unit 21 transmits sequence information for controlling the nuclear magnetic resonance imaging unit 10 to the sequence controlling unit. The interface unit 21 also receives echo data from the sequence controlling unit and stores the data in the storage unit 23.

The inputting unit 22 is a device such as a keyboard, a mouse, a button, or a switch, and inputs a signal in accordance with an operator's operation to said device.

The storage unit 23 comprises, in its configuration, a storage medium such as a hard disc, a flash memory, a RAM, or a ROM and a reading apparatus for reading information stored in the storage medium. The storage unit 23 stores echo data transmitted from the sequence controlling unit, various MRI image data generated from the echo data, reference information for predicting motor function recovery of the patient, a program for image generation and analysis, a program for controlling each function unit of the MRI apparatus 1 which is executed by the controlling unit 26, and various setting information or the like.

The computing unit 24 consists of hardware such as a CPU. The computing unit 24 reads a program stored in the storage unit 23 to reconstruct an image from echo data stored in the storage unit 23, and generates a DTI image from the reconstructed image. The computing unit 24 also analyzes a DTI image of the brain of the patient storage unit 23 and performs computation to predict motor function recovery of the patient.

The outputting unit 25 outputs various information such as an MRI image generated by the computing unit 24 or a predicted value of a motor function recovery degree obtained by performing computation to the outside of the computer 20, typically, a display connected to the outputting unit 25.

The controlling unit 26 is connected with each function unit constituting the MRI apparatus 1, and reads a program stored in the storage unit 23 to control the operation thereof. For example, the controlling unit 26 generates sequence information from an imaging condition set by an operator and transmits the sequence information to the sequence controlling unit to control imaging of the nuclear magnetic resonance imaging unit 10. In this case, the imaging condition is a set value of various DTI imaging parameters such as b value, TR, TE, NEX, voxel size, number of slices, or diffusion gradient direction. Those skilled in the art can appropriately set these values so as to be suitable for obtaining a DTI image.

Figure 2:
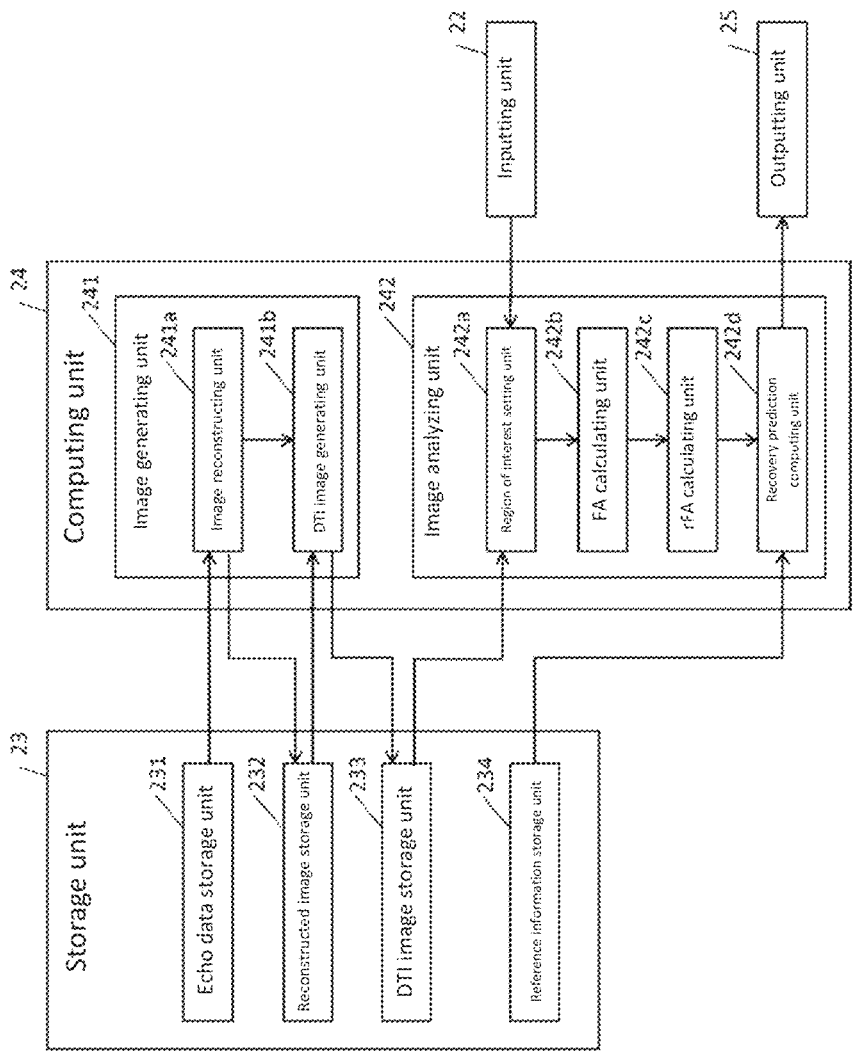
FIG. 2 is a functional block diagram showing the configuration of a storage unit, a computing unit, an inputting unit, and an outputting unit of an MRI apparatus that is one embodiment of the present disclosure.

Next, the function of the computing unit 24, including the relationship with the inputting unit 22, the storage unit 23, and the outputting unit 25, is explained while referring to FIG. 2. FIG. 2 is a functional block diagram showing the configuration of a storage unit, a computing unit, an inputting unit, and an outputting unit in one embodiment of the present disclosure. The storage unit 23 has an echo data storage unit 231, a reconstructed image storage unit 232, a DTI image storage unit 233, and a reference information storage unit 234. Further, the computing unit 24 has an image generating unit 241 and an image analyzing unit 242. Furthermore, the image generating unit 241 has an image reconstructing unit 241a and a DTI image generating unit 241b, and the image analyzing unit 242 has a region of interest setting unit 242a, an FA calculating unit 242b, an rFA calculating unit 242c, and a recovery prediction computing unit 242d.

The function of the image generating unit 241 for generating a DTI image from echo data is explained. The echo data storage unit 231 stores echo data transmitted from the sequence controlling unit for each patient. The image reconstructing unit 241a implements reconstruction processing such as Fourier transform on the echo data stored by the echo data storage unit 231, thereby generating a reconstructed image such as a diffusion weighted image (DWI image). The reconstructed image storage unit 232 stores the generated reconstructed image.

The DTI image generating unit 241b performs DTI analysis on the generated reconstructed image to generate a DTI image. In DTI analysis, diffusion coefficients $D_{xx}$, $D_{xy}$, $D_{xz}$, $D_{yy}$, $D_{yz}$, and $D_{zz}$ that are components of the diffusion tensor D represented by 3×3 symmetric matrix of Expression 1 are calculated for each voxel to diagonalize the matrix of Expression 1, thereby calculating the eigenvalues ($\lambda_1$, $\lambda_2$, and $\lambda_3$) shown in Expression 2. In this case, $D_{xx}$, $D_{yy}$, and $D_{zz}$ are diffusion coefficients of when a gradient magnetic field is applied in the x axis direction, the y axis direction, and the z axis direction, respectively, of the MRI apparatus coordinate system.

[Numeral 1]

$$D = \begin{pmatrix} D_{xx} & D_{xy} & D_{xz} \\ D_{yx} & D_{yy} & D_{yz} \\ D_{zx} & D_{zy} & D_{zz} \end{pmatrix} \qquad \text{Expression 1}$$

[Numeral 2]

$$D = \begin{pmatrix} \lambda_1 & 0 & 0 \\ 0 & \lambda_2 & 0 \\ 0 & 0 & \lambda \end{pmatrix} \qquad \text{Expression 2}$$

ADC (apparent diffusion coefficient) and FA (fractional anisotropy) that are parameters of the diffusion tensor are calculated from the calculated eigenvalues ($\lambda_1$, $\lambda_2$, and $\lambda_3$) (Expressions 3 and 4).

[Numeral 3]

$$ADC = \frac{\lambda_1 + \lambda_2 + \lambda_3}{3} = \langle D \rangle \qquad \text{Expression 3}$$

[Numeral 4]

$$FA = \sqrt{\frac{3}{2}} \frac{\sqrt{(\lambda_1 - \langle D \rangle)^2 + (\lambda_2 - \langle D \rangle)^2 + (\lambda_3 - \langle D \rangle)^2}}{\sqrt{\lambda_1^2 + \lambda_2^2 + \lambda_3^2}} \qquad \text{Expression 4}$$

The DTI image generating unit 241b maps these parameters to generate a DTI image such as $\lambda_1$ map, $\lambda_2$ map, $\lambda_3$ map, ADC map, or FA map. The DTI image storage unit 233 stores the generated DTI image.

Figure 3:
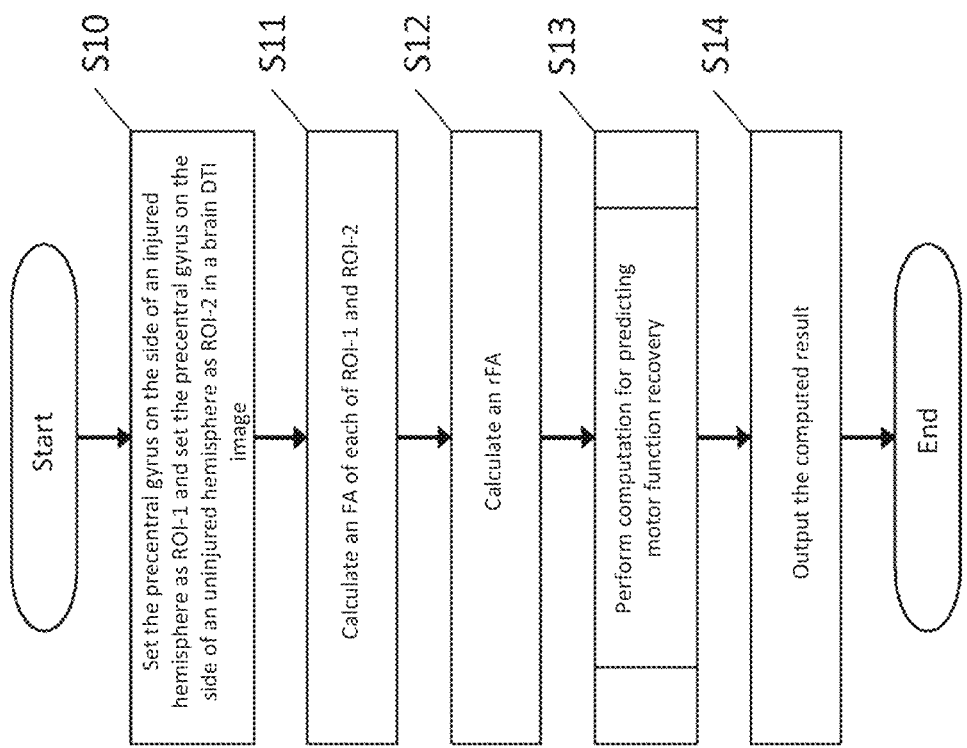
FIG. 3 is a flowchart showing each step in a prediction method that is one embodiment of the present disclosure.
Figure 4:
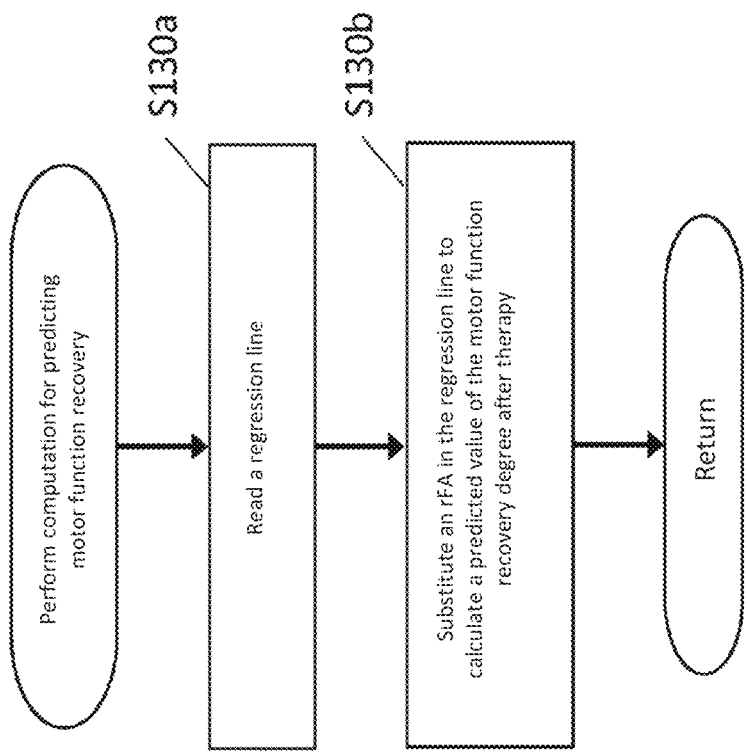
FIG. 4 is a flowchart showing the detail of the computing step in a prediction method that is one embodiment of the present disclosure.
Figure 5:
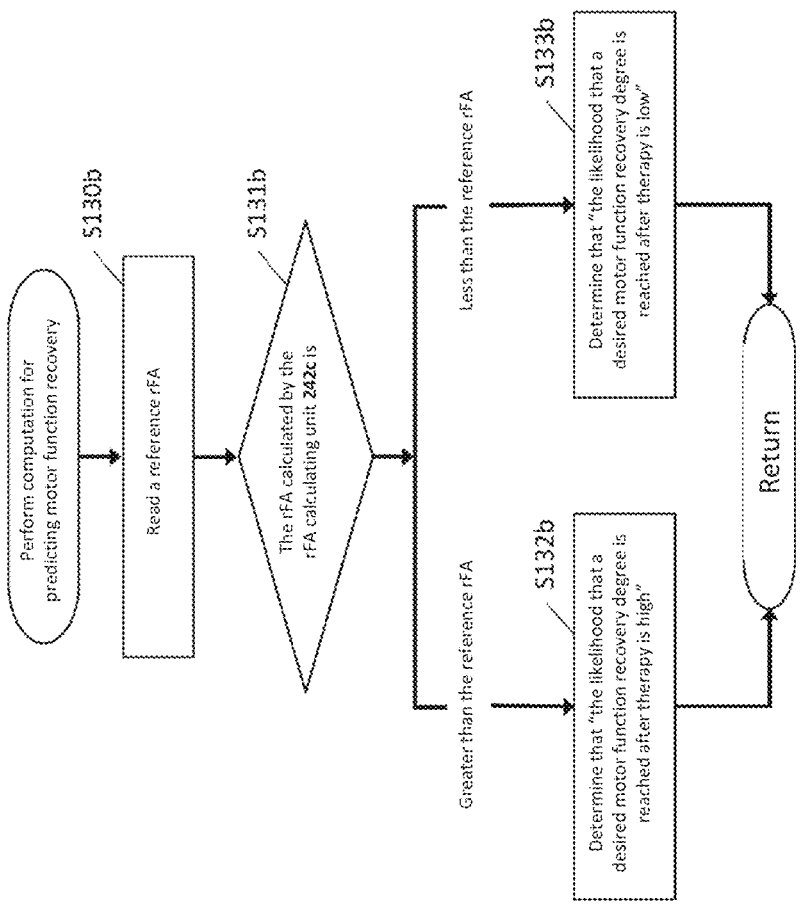
FIG. 5 is a flowchart showing the detail of the computing step in a prediction method that is one embodiment of the present disclosure.

Subsequently, the function of the image analyzing unit 242 for analyzing a DTI image to perform recovery prediction computation is explained in accordance with a method for predicting motor function recovery after regeneration therapy of a patient having a brain focal injury which is one embodiment of the present disclosure while referring to FIGS. 2 to 5. FIG. 3 is a flowchart showing each step in a prediction method that is one embodiment of the present disclosure, wherein the method is implemented using each of the above-described function units. FIGS. 4 and 5 are each a flowchart showing the detail of the computing step in the prediction method.

The region of interest setting unit 242a sets a first region of interest (ROI-1) in a position corresponding to the precentral gyrus on the side of an injured hemisphere and sets a second region of interest (ROI-2) in a position corresponding to the precentral gyrus on the side of an uninjured hemisphere on the DTI image stored in the DTI image storage unit 233, typically on an FA map (step S10). The ROI may be manually set based on an anatomical position, may be set while being superposed with another medical image, or may be automatically set based on the function of known DTI image analysis software. When the ROI is manually set, an operation to set the ROI by an operator is accepted via the inputting unit 22.

The FA calculating unit 242b calculates an injured hemisphere-side FA and an uninjured hemisphere-side FA that are the FA in the ROI-1 and the ROI-2, respectively (step S11). The injured hemisphere-side FA and the uninjured hemisphere-side FA are the mean value of the FA of all voxels contained in the ROI-1 and the ROI-2, respectively.

The rFA calculating unit 242c calculates an rFA represented by the injured hemisphere-side FA/the uninjured hemisphere-side FA (step S12).

The recovery prediction computing unit 242d performs computation for predicting motor function recovery of the patient after regeneration therapy based on the rFA calculated by the rFA calculating unit 242c (step S13) and outputs the computed result to the outputting unit 25 (step S14). The computation for predicting motor function recovery is performed based on the reference information stored in the reference information storage unit 234 in addition to the calculated rFA.

In a certain embodiment, reference information is a regression line which is prepared in advance and has an rFA of a patient having a brain focal injury prior to regeneration therapy and a motor function recovery degree of the same patient after the therapy as variables. In this case, the motor function recovery degree is an extent of recovery of a motor function by therapy which is evaluated using a known evaluation method capable of evaluating a motor function (e.g., Barthel Index (BI), Fugl-Meyer Assessment (FMA), or the like). The motor function recovery degree can be represented as a difference between the score prior to the therapy and the score after the therapy in the same patient.

In another embodiment, reference information is a reference rFA which is prepared in advance. The reference rFA is a cutoff value to distinguish a patient having a brain focal injury who is likely to obtain a desired motor function recovery degree after regeneration therapy and a patient having a brain focal injury who is likely not to obtain a desired motor function recovery degree.

As shown in the Examples below, the present inventors have found that a motor function recovery degree after regeneration therapy is correlated with an rFA prior to the therapy in a patient having a brain focal injury. Thus, it is possible to predict motor function recovery after regeneration therapy of a patient who is going to receive the therapy from now by referring to an rFA calculated from a brain DTI image prior to regeneration therapy and a motor function recovery degree after the therapy of a patient who already received the therapy. It is also possible to evaluate whether this patient is likely to be adapted to regeneration therapy, in other words, whether regeneration therapy can be expected to be effective.

Specifically, for example, a regression line having an rFA calculated from a brain DTI image prior to regeneration therapy and a motor function recovery degree after the therapy of a patient who already received the therapy as variables is prepared in advance, and an rFA calculated from a brain DTI image of a subject patient who is going to receive regeneration therapy from now is substituted in this regression line, whereby a predicted value of the motor function recovery degree after regeneration therapy of the subject patient can be calculated (steps S130a and S130b).

Similarly, for example, rFA an prior to therapy corresponding to a desired motor function recovery degree is determined as a reference rFA in advance based on a scatter diagram or a regression line having an rFA calculated from a brain DTI image prior to regeneration therapy and a motor function recovery degree after the therapy of a patient who already received the therapy as variables, and it is determined whether an rFA calculated from a brain DTI image of a subject patient who is going to receive regeneration therapy from now exceeds the reference rFA, whereby the level of a likelihood that the subject patient reaches the desired motor function recovery degree after regeneration therapy can be calculated (steps S130b to S133b). The reference rFA can be appropriately set depending on the motor function recovery degree that is a target.

Reference information such as a regression line or a reference rFA is preferably obtained from a patient having the same type of disease as a patient who is the subject of prediction of motor function recovery after regeneration therapy. For example, if a patient who is the subject of prediction is a patient with cerebral infarction, reference information is preferably prepared by using an rFA calculated from a brain DTI image prior to regeneration therapy and a motor function recovery degree after the therapy of a patient with cerebral infarction who received the therapy.

Reference information is also preferably obtained from a patient who received the same type of therapy as the therapy to which a patient attempts to be adapted. For example, if the therapy is administration of a bone marrow mesenchymal stem cell (BMSC), reference information is preferably prepared by using an rFA calculated from a brain DTI image prior to therapy and a motor function recovery degree after the therapy of a patient administered with a BMSC.

The foregoing is the explanation of the exemplary embodiments of a method for predicting motor function recovery after regeneration therapy of a patient having a brain focal injury and an MRI apparatus that can be used in the implementation of the method. An exemplary embodiment of the image analysis apparatus of the present disclosure that can be used in the implementation of the above-described method is an apparatus having the image analyzing unit 242 of the MRI apparatus 1. The detail thereof is as described in the above explanation.

Further, the program of the present disclosure that can be used in the implementation of the above-described method is a program for causing a computer to execute each step of the above-described method. The detail thereof is as described in the above explanation. In addition, a computer readable storage medium storing the above-described program can be any storage medium such as a hard disc, a flash memory, a CD, or a DVD.

According to the present disclosure, it is possible to predict motor function recovery after regeneration therapy of a patient who is going to receive the therapy, and it is also possible to evaluate whether this patient is likely to be adapted to regeneration therapy, in other words, whether regeneration therapy can be expected to be effective. Thus, the method and the program according to the present disclosure can also be represented as a method and a program for evaluating the adaptability of a patient to regeneration therapy, or a method and a program assisting the evaluation of the adaptability of a patient to regeneration therapy. The same applies to other embodiments of the present disclosure as well.

As used herein, "brain injury" refers to some type of injury being caused to the brain and includes injury being caused to the blood vessel of the brain. The cause of the injury is not particularly limited. For example, "brain injury" includes traumatic brain injury, stroke, cerebral infarction, anoxic brain injury, brain tumor encephalitis, and the like, and can also include brain focal injury.

As used herein, "brain focal injury" refers to a state in which an injury is focally caused to the brain. "Patient having a brain focal injury" refers to a patient in which an injury is focally caused to the brain. Examples of a brain focal injury can include cerebral infarction, head trauma, and cerebral hemorrhage. In the present disclosure, a patient having a brain focal injury is not restricted as long as the patient is a patient in which an injury is focally caused to the brain and whose motor function is damaged, and said patient may be a patient in any stage of the acute stage, the sub-acute stage, and the chronic stage.

As used herein, "regeneration therapy of a patient having a brain focal injury" means therapy for regenerating an injured nervous system cell of a patient and recovering various function disorders caused by the injury by using a cell of the patient himself/herself (autologous) or others (allogeneic) or a secretion thereof.

A cell that can be used for regeneration therapy of a patient having a brain focal injury may be any cell having differentiation potency into a nervous system cell. Examples can include a stem cell having pluripotency such as a mesenchymal stem cell and a neural stem cell and a pluripotent stem cell such as an induced pluripotent stem cell (iPS cell), an embryonic stem cell (ES cell), an embryonic carcinoma cell (EC cell), and an embryonic germ cell (EG cell). In the present disclosure, a cell that is preferably used for therapy is a mesenchymal stem cell, particularly a bone marrow mesenchymal stem cell (BMSC; also called bone marrow stem cell).

It is believed that the cell exemplified above produces a therapeutic effect by differentiation into a nervous system cell of the transplanted cell itself (transdifferentiation) and by activation and nerve repair promotion (nursing effect) of a neural stem cell of a patient himself/herself by a cytokine, a trophic factor, an exosome or the like contained in a secretion from the transplanted cell. Thus, a secretion of the cell exemplified above (e.g., an exosome, a cell culture supernatant or the like derived from said cell) can also be used for therapy in the present disclosure.

The above-described cell and the secretion thereof can be prepared by a known method using a biological sample separated from a patient himself/herself or others. A stem cell having pluripotency may be a cell obtained by inducing differentiation of a pluripotent stem cell.

The dosage and the route of administration of the above-described cell and the secretion thereof are appropriately set by those skilled in the art while referring to a known dosing regimen relating to those dosage and route of administration. For example, $10^4$ to $10^9$ cells, preferably $10^5$ to $10^8$ cells, per kg of a patient's body weight can be administered to the patient by systemic administration such as intravenous administration or intra-arterial administration, or $10^2$ to $10^9$ cells, preferably $10^4$ to $10^6$ cells, per kg of the patient's body weight can be administered to the patient by local administration such as intracerebral direct administration or intrathecal administration one or multiple times.

As used herein, "or" is used when "at least one or more" of the listed matters in the sentence can be employed. When explicitly described herein as "within the range" of "two values", the range also includes the two values themselves. Reference literatures such as scientific literatures, patents, and patent applications cited herein are incorporated herein by reference to the same extent that the entirety of each document is specifically described.

As described above, the present disclosure has been explained while showing preferred embodiments to facilitate understanding. The present disclosure is explained hereinafter based on Examples. The above explanation and the following Examples are not provided to limit the present disclosure, but for the sole purpose of exemplification. Thus, the scope of the present disclosure is not limited to the embodiments and Examples specifically described herein and is limited only by the scope of claims.

EXAMPLES

Example 1: Evaluation of a State of a Motor Function with DTI

With approval by the Institutional Review Board of Hokkaido University Hospital, the following study was implemented.
(1) Subject Patient Six patients in an acute stage (early in the onset) of cerebral infarction who meet the following five criteria: the patient was 20 years old or older and under 80 years old when the consent was obtained; 14 days or less had passed from the onset of cerebral infarction when the consent was obtained; cerebral infarction was caused to the perfused area of the internal carotid artery; mRS before the onset of cerebral infarction is 0 or 1; the patient has a moderate to severe neurological symptom (NIHSS (National Institutes of Health Stroke Scale): ≥6) (provided that the total score of the items "5. Motor Arm" and "6. Motor Leg" of NIHSS is 6 or more), who do not violate the predetermined exclusion criteria, and who agreed to the present study were selected as the subjects. Five patients out of six were patients with hemorrhagic infarction, in other words, cerebral infarction with cerebral hemorrhage.
(2) Preparation and Administration of a Bone Marrow Stem Cell After the case registration, the bone marrow of the patients was promptly collected, and cell culture and bone marrow stem cell preparation were carried out in the Cell Processing Center of the Clinical Research and Medical Innovation Center of Hokkaido University Hospital. The prepared bone marrow stem cells (20,000,000 or 50,000,000 cells/patient) were directly administered to the brain of the patients after 3 to 5 weeks from the collection of the bone marrow.

(3) Motor Function Evaluation

The motor function of the patients was evaluated with Barthel Index (BI) and Fugl-Meyer Assessment (FMA). The section of stroke rehabilitation evaluation in the Japanese Guideline for the Management of Stroke 2015 issued by the Japan Stroke Society recommends using these indicators. The motor function was evaluated as of the case registration (after 14 days from cerebral infarction), 7 days before the cell administration (after 50 days in average from cerebral infarction), after 1 month from the cell administration, after 3 months from the cell administration, after 6 months from the cell administration, and after 12 months from the cell administration. ΔBI and ΔFMA obtained by subtracting the score of BI and FMA in the sub-acute stage when the acute stage therapy was almost complete (on day 10 to day 50 after the onset of cerebral infarction; hereinafter referred to as the sub-acute stage) from the score of BI and FMA at the 12th month after the cell administration (the 6th month for the patients who did not reach the 12th month as of the application (Female E and Female F); hereinafter referred to as the chronic stage) were used as the motor function recovery degree.

(4) DTI Imaging

A DTI image of the brain of each of the patients was imaged in the period corresponding to the sub-acute stage and the chronic stage. Imaging was performed by using an MRI apparatus (3T Achieva TX (Philips Medical Systems)) with default setting (b=0, 1000 s mm$^{-2}$, TR/TE=5032/85 msec, NEX=1, voxel size=3×3×3 mm$^3$, no. of slices=43, 32 diffusion gradient directions).

(5) Image Analysis

Image analysis software (MRFiber Trak, Extended MR Work Space version 2.6.3.4) accompanying the MRI apparatus was used to analyze the DTI image using default setting except for changing minimal FA from 0.15 to 0.18 and changing maximum angle change to 25°.

ROI was set to one portion, two portions, or all of the precentral gyrus, the posterior limb of the internal capsule, and the pons for each of the left hemisphere and the right hemisphere to calculate an FA, and the FA on the infarction hemisphere-side ROI was divided by the FA on the non-infarction hemisphere-side ROI to calculate an rFA. The ROI was set to the precentral gyrus based on an anatomical position. The ROI was set to each of the posterior limb of the internal capsule and the pons so as to include a site corresponding to the corticospinal tract (the site in which the FA becomes greater in the z-axis (craniocaudal) direction) displayed on a color map by diffusion tensor tractography (DTT) analysis in addition to an anatomical position. In DTT analysis, Minimum fiber length was 10 mm.

(6) Result

Figure 6:
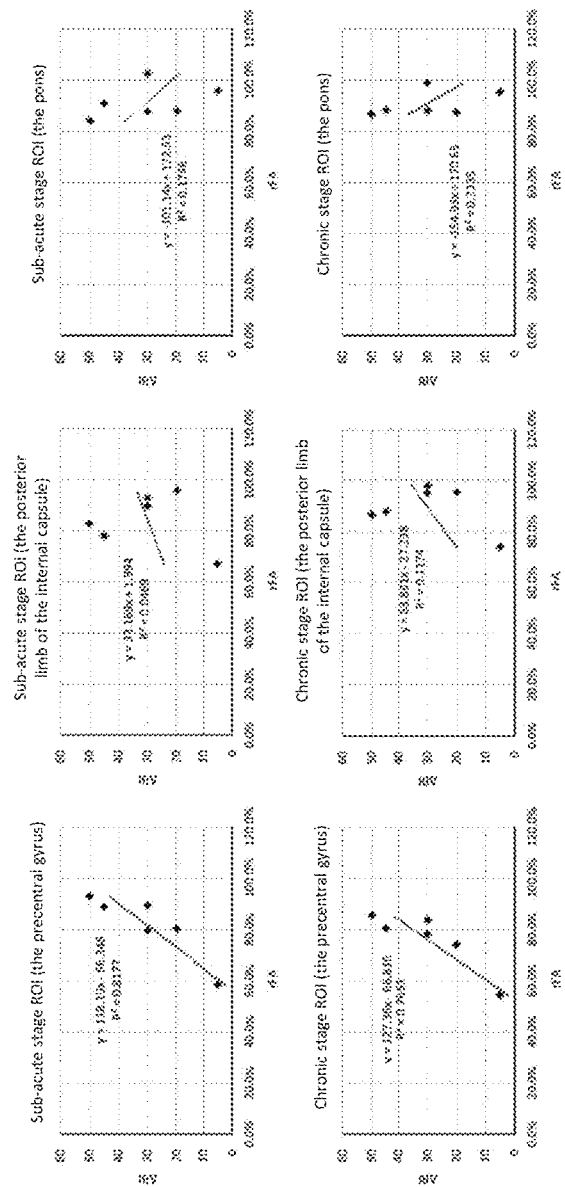
FIG. 6 is a scatter diagram plotting: the rFA calculated by setting the ROI to any one portion of the precentral gyrus, the posterior limb of the internal capsule, and the pons in a brain DTI image of a patient with cerebral infarction; and the motor function recovery degree ΔBI of the patient.
Figure 7:
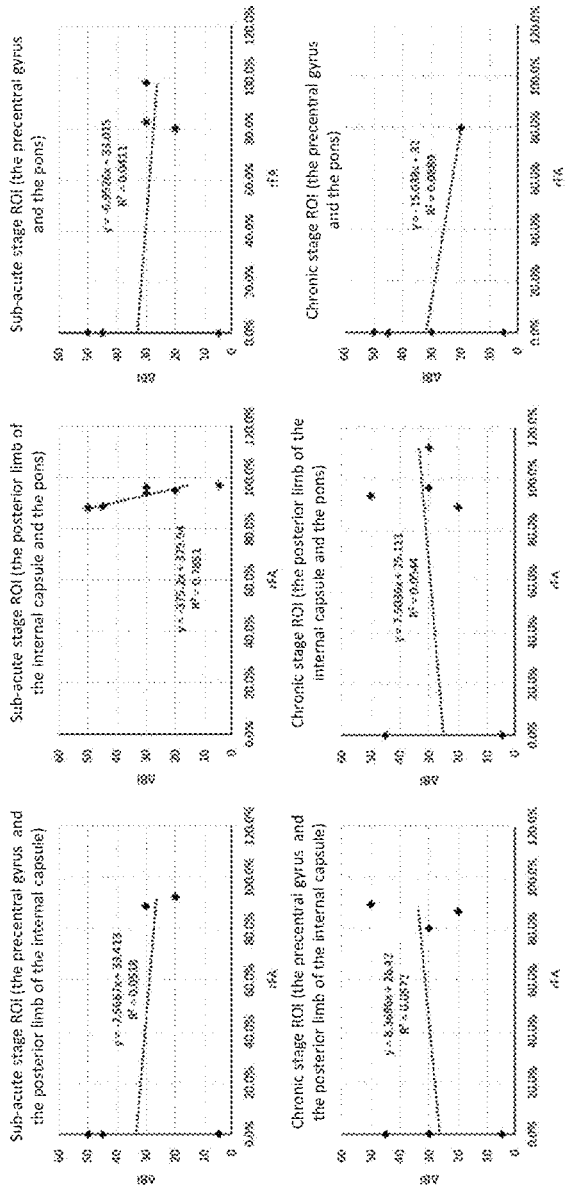
FIG. 7 is a scatter diagram plotting: the rFA calculated by setting the ROI to any two portions of the precentral gyrus, the posterior limb of the internal capsule, and the pons in a brain DTI image of a patient with cerebral infarction; and the motor function recovery degree ΔBI of the patient.
Figure 8:
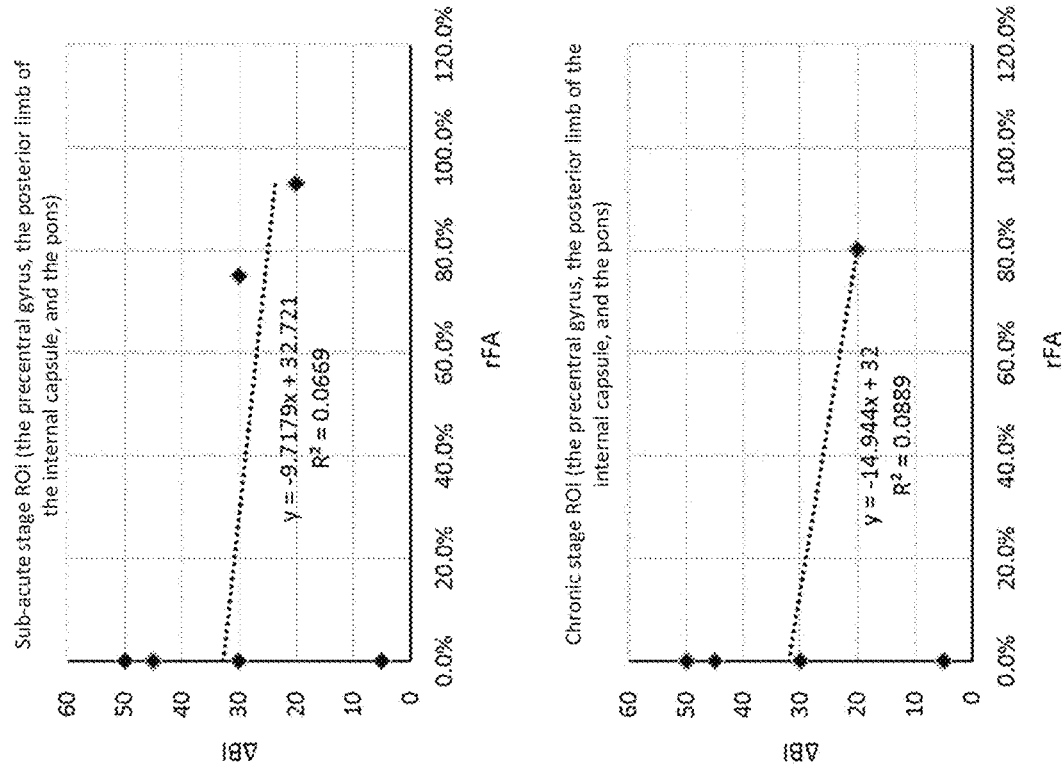
FIG. 8 is a scatter diagram plotting: the rFA calculated by setting the ROI to three portions, the precentral gyrus, the posterior limb of the internal capsule, and the pons in a brain DTI image of a patient with cerebral infarction; and the motor function recovery degree ΔBI of the patient.
Figure 9:
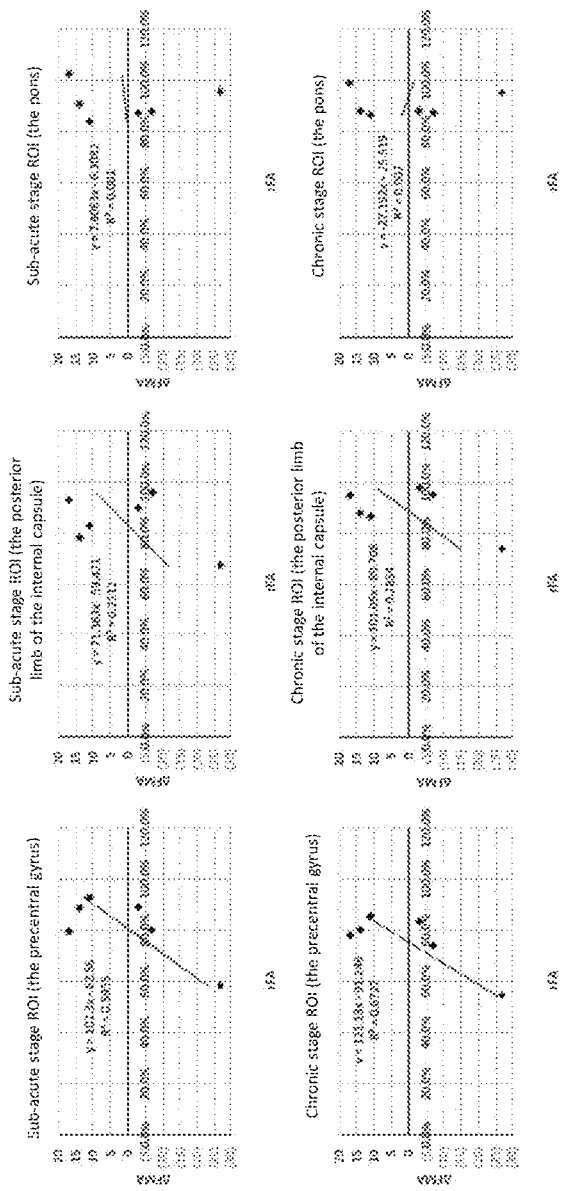
FIG. 9 is a scatter diagram plotting: the rFA calculated by setting the ROI to any one portion of the precentral gyrus, the posterior limb of the internal capsule, and the pons in a brain DTI image of a patient with cerebral infarction; and the motor function recovery degree ΔFMA of the patient.
Figure 10:
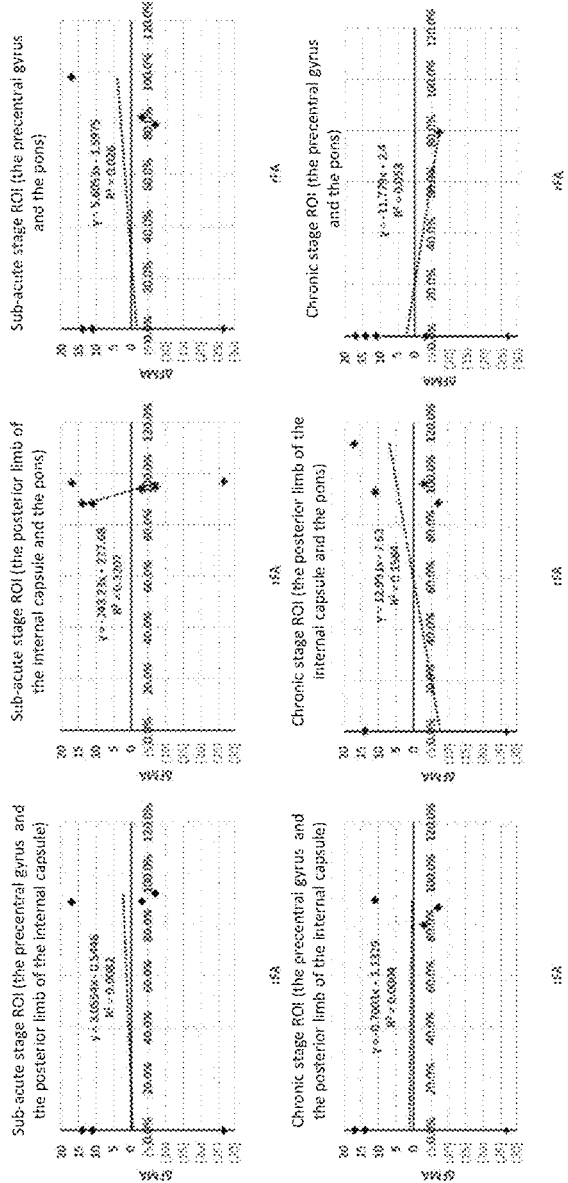
FIG. 10 is a scatter diagram plotting: the rFA calculated by setting the ROI to any two portions of the precentral gyrus, the posterior limb of the internal capsule, and the pons in a brain DTI image of a patient with cerebral infarction; and the motor function recovery degree ΔFMA of the patient.
Figure 11:
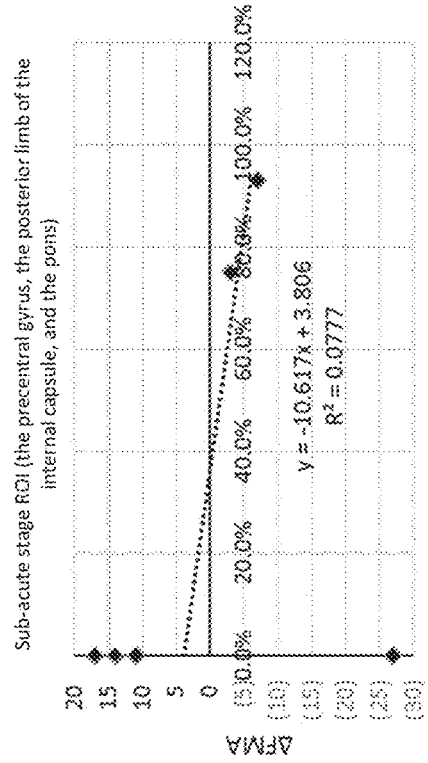
FIG. 11 is a scatter diagram plotting: the rFA calculated by setting the ROI to three portions, the precentral gyrus, the posterior limb of the internal capsule, and the pons in a brain DTI image of a patient with cerebral infarction; and the motor function recovery degree ΔFMA of the patient.
Figure 11:
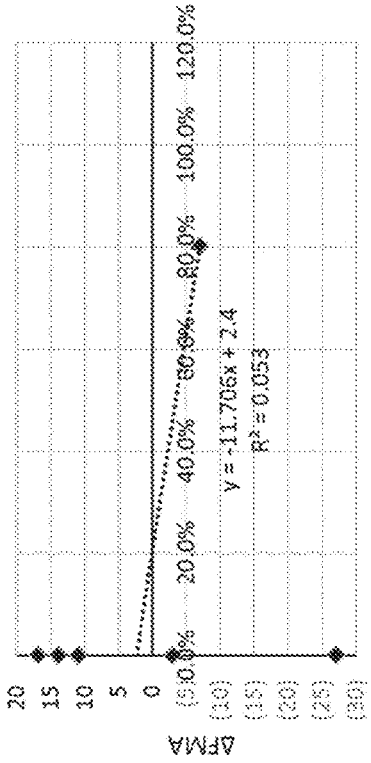

Table 1 shows the result of evaluation of the motor function including the background of the patients and the DTI imaging period. In addition, Tables 2 to 4 show the calculated FA and rFA, FIGS. 6 to 8 show a scatter diagram plotting the rFA and the motor function recovery degree ΔBI, and FIGS. 9 to 11 show a scatter diagram plotting the rFA and the motor function recovery degree ΔFMA. "-" in the tables indicates that an FA beyond the threshold was not calculated.

While correlation was observed between the rFA and the ΔBI when the ROI was set to only the precentral gyrus (correlation coefficient: sub-acute stage $R^2$=0.82, chronic stage $R^2$=0.77), no correlation was observed when the ROI was set to only the posterior limb of the internal capsule or the pons ($R^2$=0.05 to 0.23). Also, no correlation was observed when the ROI was set to any two portions or three portions of the precentral gyrus, the posterior limb of the internal capsule, and the pons ($R^2$=0.05 to 0.09, however, although inverse correlation, 0.78, was shown when the ROI was set to two portions of the posterior limb of the internal capsule and the pons, it was determined that it is impossible to actually predict recovery of the patients due to a small variation in the rFA value).

Similarly, while correlation was also observed between the rFA and the ΔFMA only when the ROI was set to only the precentral gyrus (correlation coefficient: sub-acute stage $R^2$=0.60, chronic stage $R^2$=0.67), no correlation was observed when the ROI was set to only the posterior limb of the internal capsule or the pons ($R^2$=0.00 to 0.29). Also, no correlation was observed when the ROI was set to any two portions or three portions of the precentral gyrus, the posterior limb of the internal capsule, and the pons ($R^2$=0.05 to 0.30).

TABLE 1

| Patient | Age | Injured hemisphere | Hemorrhagic infarction (cerebral hemorrhage) | The number of days after onset as of DTi imaging (sub-acute stage) | The numbrer of days after onset as of DTi imaging (chronic stage) | Δ BI | Δ FMA |
|---|---|---|---|---|---|---|---|
| Female A | 70s | Right | X | 14 days | 410 days | 30 | −3 |
| Male B | 60s | Right | ○ | 46 days | 410 days | 30 | 17 |
| Male C | 50s | Left | ○ | 10 days | 387 days | 5 | −27 |
| Male D | 60s | Left | ○ | 14 days | 395 days | 20 | −7 |
| Female E | 60s | Right | ○ | 14 days | 227 days | 45 | 14 |
| Female F | 60s | Left | ○ | 15 days | 242 days | 50 | 11 |

TABLE 2

Sub-acute stage

| Patient | ROI (the precentral gyrus) | | | ROI (the posterior limb of the internal capsule) | | | ROI (the pons) | | |
|---|---|---|---|---|---|---|---|---|---|
| | Left hemisphere-side FA | Right hemisphere-side FA | rFA | Left hemisphere-side FA | Right hemisphere-side FA | rFA | Left hemisphere-side FA | Right hemisphere-side FA | rFA |
| Female A | 0.426 ± 0.159 | 0.380 ± 0.136 | 89.2% | 0.476 ± 0.182 | 0.427 ± 0.172 | 89.7% | 0.545 ± 0.189 | 0.477 ± 0.184 | 87.5% |
| Male B | 0.414 ± 0.153 | 0.329 ± 0.11 | 79.5% | 0.478 ± 0.170 | 0.460 ± 0.182 | 93.0% | 0.514 ± 0.188 | 0.493 ± 0.188 | 102.7% |
| Male C | 0.256 ± 0.078 | 0.439 ± 0.163 | 58.3% | 0.345 ± 0.145 | 0.514 ± 0.169 | 67.1% | 0.513 ± 0.188 | 0.535 ± 0.179 | 95.9% |
| Male D | 0.376 ± 0.165 | 0.469 ± 0.177 | 80.2% | 0.466 ± 0.177 | 0.486 ± 0.176 | 95.9% | 0.478 ± 0.178 | 0.544 ± 0.176 | 87.9% |
| Female E | 0.451 ± 0.171 | 0.401 ± 0.153 | 88.9% | 0.494 ± 0.173 | 0.386 ± 0.158 | 78.1% | 0.516 ± 0.175 | 0.469 ± 0.178 | 90.9% |
| Female F | 0.419 ± 0.157 | 0.450 ± 0.177 | 93.0% | 0.418 ± 0.159 | 0.505 ± 0.175 | 82.8% | 0.450 ± 0.174 | 0.536 ± 0.188 | 84.0% |

Chronic stage

| Patient | ROI (the precentral gyrus) | | | ROI (the posterior limb of the internal capsule) | | | ROI (the pons) | | |
|---|---|---|---|---|---|---|---|---|---|
| | Left hemisphere-side FA | Right hemisphere-side FA | rFA | Left hemisphere-side FA | Right hemisphere-side FA | rFA | Left hemisphere-side FA | Right hemisphere-side FA | rFA |
| Female A | 0.427 ± 0.156 | 0.357 ± 0.13 | 83.6% | 0.481 ± 0.182 | 0.472 ± 0.178 | 98.1% | 0.556 ± 0.180 | 0.490 ± 0.174 | 88.1% |
| Male B | 0.415 ± 0.156 | 0.324 ± 0.111 | 78.1% | 0.450 ± 0.171 | 0.428 ± 0.171 | 95.1% | 0.525 ± 0.191 | 0.530 ± 0.226 | 99.0% |
| Male C | 0.246 ± 0.099 | 0.451 ± 0.169 | 54.5% | 0.372 ± 0.144 | 0.502 ± 0.172 | 74.1% | 0.517 ± 0.199 | 0.542 ± 0.174 | 95.4% |
| Male D | 0.334 ± 0.105 | 0.451 ± 0.158 | 74.1% | 0.468 ± 0.164 | 0.490 ± 0.170 | 95.5% | 0.468 ± 0.156 | 0.535 ± 0.171 | 87.4% |
| Female E | 0.436 ± 0.166 | 0.350 ± 0.137 | 80.3% | 0.504 ± 0.178 | 0.444 ± 0.193 | 88.1% | 0.504 ± 0.178 | 0.444 ± 0.193 | 88.1% |
| Female F | 0.384 ± 0.149 | 0.449 ± 0.172 | 85.5% | 0.437 ± 0.163 | 0.504 ± 0.179 | 86.7% | 0.437 ± 0.163 | 0.504 ± 0.179 | 86.7% |

TABLE 3

Sub-acute stage

| Patient | ROI (the precentral gyrus and the posterior limb of the internal capsule) | | | ROI (the posterior limb of the internal capsule and the pons) | | | ROI (the precentral gyrus and the pons) | | |
|---|---|---|---|---|---|---|---|---|---|
| | Left hemisphere-side FA | Right hemisphere-side FA | rFA | Left hemisphere-side FA | Right hemisphere-side FA | rFA | Left hemisphere-side FA | Right hemisphere-side FA | rFA |
| Female A | 0.490 ± 0.186 | 0.437 ± 0.168 | 89.2% | 0.492 ± 0.183 | 0.463 ± 0.184 | 94.1% | 0.490 ± 0.186 | 0.402 ± 0.163 | 82.4% |
| Male B | 0.464 ± 0.182 | 0.413 ± 0.168 | 89.0% | 0.467 ± 0.184 | 0.484 ± 0.188 | 96.5% | 0.504 ± 0.196 | 0.494 ± 0.177 | 98.0% |
| Male C | — | 0.492 ± 0.178 | 0.0% | 0.471 ± 0.193 | 0.485 ± 0.181 | 97.1% | — | 0.514 ± 0.183 | 0.0% |
| Male D | 0.438 ± 0.174 | 0.474 ± 0.180 | 92.4% | 0.456 ± 0.180 | 0.480 ± 0.181 | 95.0% | 0.461 ± 0.174 | 0.491 ± 0.183 | 79.8% |
| Female E | 0.491 ± 0.183 | — | 0.0% | 0.475 ± 0.180 | 0.421 ± 0.178 | 88.6% | 0.519 ± 0.178 | — | 0.0% |
| Female F | — | 0.508 ± 0.187 | 0.0% | 0.446 ± 0.179 | 0.505 ± 0.175 | 88.3% | — | 0.535 ± 0.195 | 0.0% |

Chronic stage

| Patient | ROI (the precentral gyrus and the posterior limb of the internal capsule) | | | ROI (the posterior limb of the internal capsule and the pons) | | | ROI (the precentral gyrus and the pons) | | |
|---|---|---|---|---|---|---|---|---|---|
| | Left hemisphere-side FA | Right hemisphere-side FA | rFA | Left hemisphere-side FA | Right hemisphere-side FA | rFA | Left hemisphere-side FA | Right hemisphere-side FA | rFA |
| Female A | 0.484 ± 0.178 | 0.388 ± 0.141 | 80.2% | 0.512 ± 0.181 | 0.494 ± 0.187 | 96.5% | 0.556 ± 0.169 | — | 0.0% |
| Male B | 0.462 ± 0.177 | — | 0.0% | 0.459 ± 0.176 | 0.514 ± 0.195 | 112.0% | 0.487 ± 0.180 | — | 0.0% |
| Male C | — | 0.499 ± 0.182 | 0.0% | — | 0.499 ± 0.181 | 0.0% | — | 0.539 ± 0.179 | 0.0% |
| Male D | 0.426 ± 0.160 | 0.490 ± 0.176 | 86.9% | 0.446 ± 0.158 | 0.501 ± 0.171 | 89.0% | 0.418 ± 0.123 | 0.524 ± 0.169 | 79.8% |
| Female E | 0.493 ± 0.198 | — | 0.0% | 0.481 ± 0.19 | — | 0.0% | 0.507 ± 0.202 | — | 0.0% |
| Female F | 0.432 ± 0.165 | 0.482 ± 0.182 | 89.6% | 0.465 ± 0.165 | 0.498 ± 0.181 | 93.4% | — | 0.505 ± 0.174 | 0.0% |

TABLE 4

ROI (the precentral gyrus, the posterior limb of the internal capsule, and the pons)

| Patient | Left hemisphere-side FA | Right hemisphere-side FA | rFA |
|---|---|---|---|
| Sub-acute stage | | | |
| Female A | 0.536 ± 0.187 | 0.402 ± 0.162 | 75.0% |
| Male B | 0.501 ± 0.193 | — | 0.0% |
| Male C | — | 0.502 ± 0.177 | 0.0% |
| Male D | 0.454 ± 0.170 | 0.488 ± 0.183 | 93.0% |
| Female E | 0.499 ± 0.183 | — | 0.0% |
| Female F | — | 0.536 ± 0.198 | 0.0% |
| Chronic stage | | | |
| Female A | 0.560 ± 0.166 | — | 0.0% |
| Male B | 0.499 ± 0.188 | — | 0.0% |
| Male C | — | 0.535 ± 0.180 | 0.0% |
| Male D | 0.419 ± 0.129 | 0.522 ± 0.169 | 80.3% |
| Female E | 0.509 ± 0.200 | — | 0.0% |
| Female F | — | 0.516 ± 0.183 | 0.0% |

Example 2: Evaluation of a State of a Motor Function with DKI

Diffusion kurtosis imaging (DKI) method was used to obtain an index of a diffusion image capable of predicting the therapeutic effect of cell administration in a patient with cerebral infarction precisely and without relying on the experience of the measurer or the like. In the present example, after a map of main indexes according to diffusion kurtosis imaging (DKI) method was created and converted into a standard brain, the value of each of the precentral gyrus on both sides and the posterior limb of the internal capsule was measured.

Figure 12:
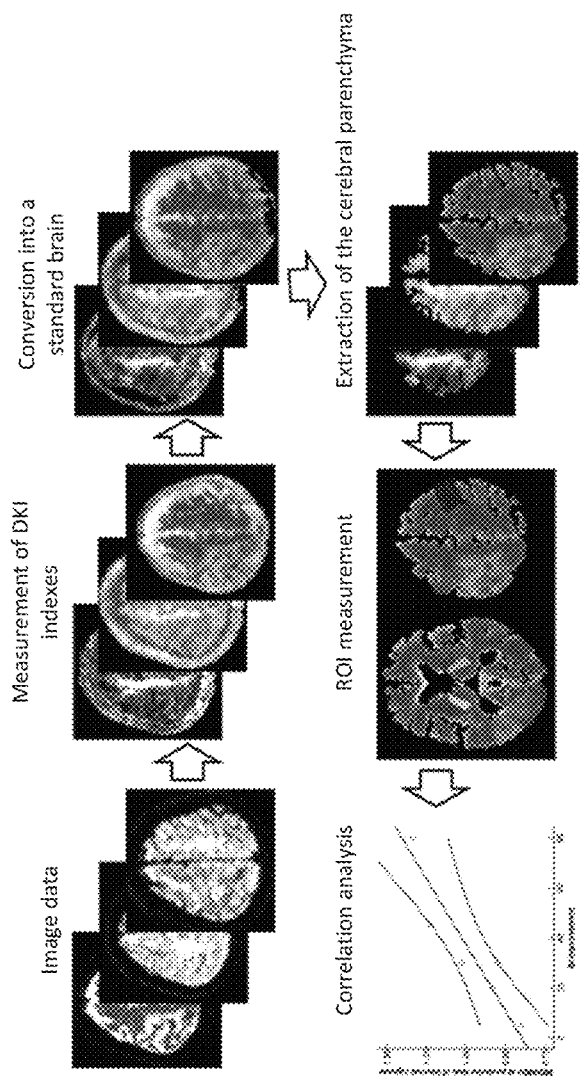
FIG. 12 is a schematic diagram showing the procedure of image processing by DKI in one embodiment of the present disclosure.

Main DKI indexes, mean kurtosis (MK), axial kurtosis (AK), radial kurtosis (RK), fractional anisotropy (FA), kurtosis fractional anisotropy (KFA), mean diffusivity (MD), axial diffusivity (AD), and radial diffusivity (RD), were calculated for each voxel (DKE2.6, MUSC Center for Biomedical Imaging, South Carolina, USA)) from diffusion image data (TR/TE=5032/85 msec, voxel size=3×3×3 mm$^3$, plane=axial, no. of slices=43, interslice gap=0 mm, b=0, 1000, 2000 sec mm$^{-2}$, NSA=1, MPG directions=32) obtained from a 3T MRI apparatus (AchievaTX, Philips Medical Systems, Best, the Netherlands). Next, conversion into the standard brain was performed using SPM12 (Wellcome Centre for Human Neuroimaging, London, UK). The regions other than the cerebral parenchyma were removed by segmentation using the anatomical image of each patient (3D-SSFP image in this study). ROI was used for the left and right precentral gyri, which are sites where the corticospinal tract runs, to measure the main DKI indexes of these regions by IBASPM Atlas (http://www.thomaskoenig.ch/Lester/ibaspm.htm) and JHU white-matter tractography Atlas (http://cmrm.med.jhmi.edu/). The ratio between the DKI indexes on the lesion side and those on the healthy side (lesion/healthy) at the point of time prior to the cell administration (after 10 to 47 days from the onset of cerebral infarction, mean=19.0±13.8 days) was calculated, and the correlation with the change (after 1 year from the cell administration-prior to the cell administration) in Barthel index (BI), modified Rankin Scale (mRS), National Institute of Health Stroke Scale (NIHSS), and functional independence measure (FIM) indicating the extent of function recovery was evaluated (FIG. 12). The number of days from the onset of cerebral infarction and the MRI imaging was used as a suppressor variable.

Table 5 shows the correlation between the diffusion image data prior to the cell administration and the function recovery degree.

TABLE 5

| Index | | FA Precentral gyrus |
|---|---|---|
| ROI | | |
| NIHSS | r | −0.23 |
| | P | 0.70 |
| mRS | r | −0.89 |
| | P | 0.04 |
| FIM | r | 0.75 |
| | P | 0.14 |
| BI | r | 0.58 |
| | P | 0.30 |

Figure 13:
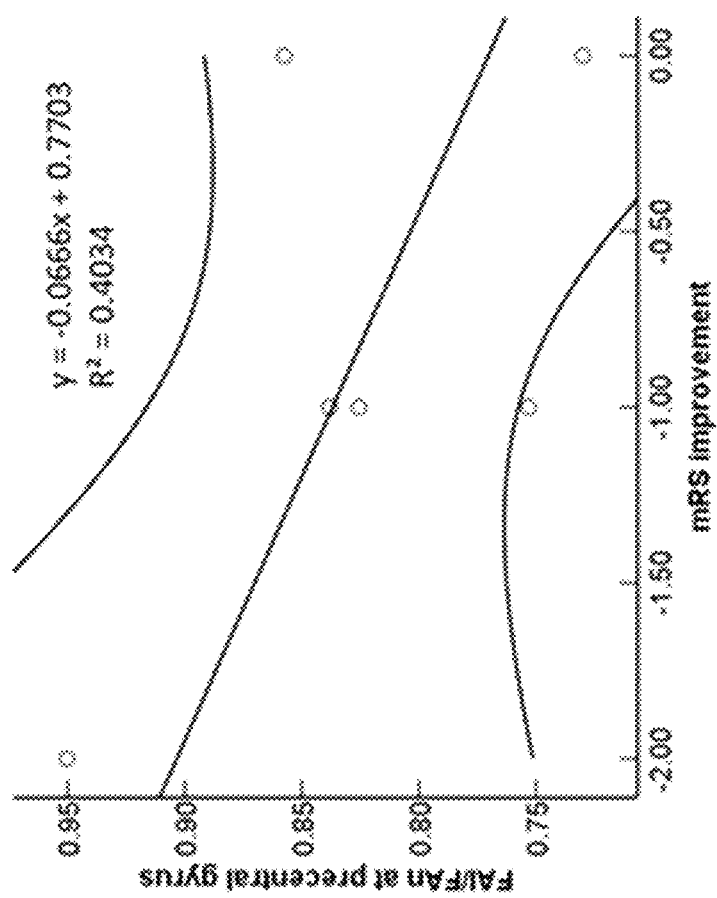
FIG. 13 is a graph showing the correlation between the ratio between FA of the precentral gyrus on the lesion side and that on the healthy side (lesion/healthy) and the change in mRS according to DKI in one embodiment of the present disclosure.
Figure 14A:
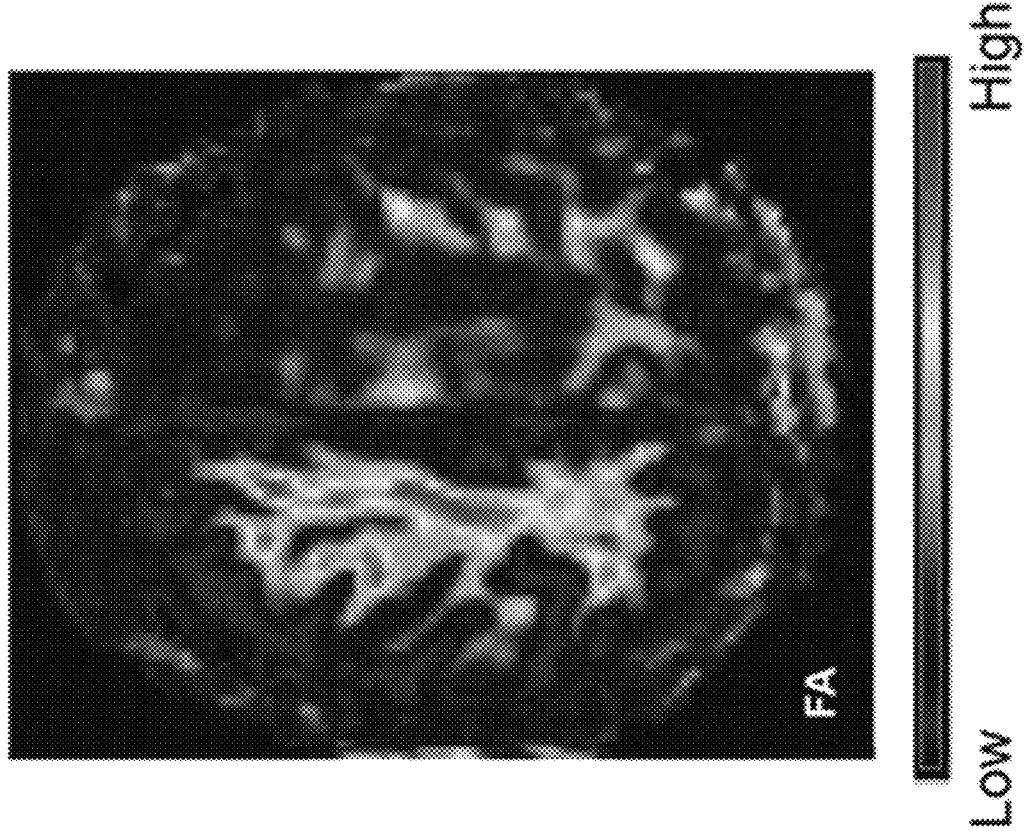
FIG. 14A is a picture showing the case of cerebral infarction in the left cerebral hemisphere with poor function recovery. The picture indicates that the FA in the left precentral gyrus is lower than that on the right side.
Figure 14B:
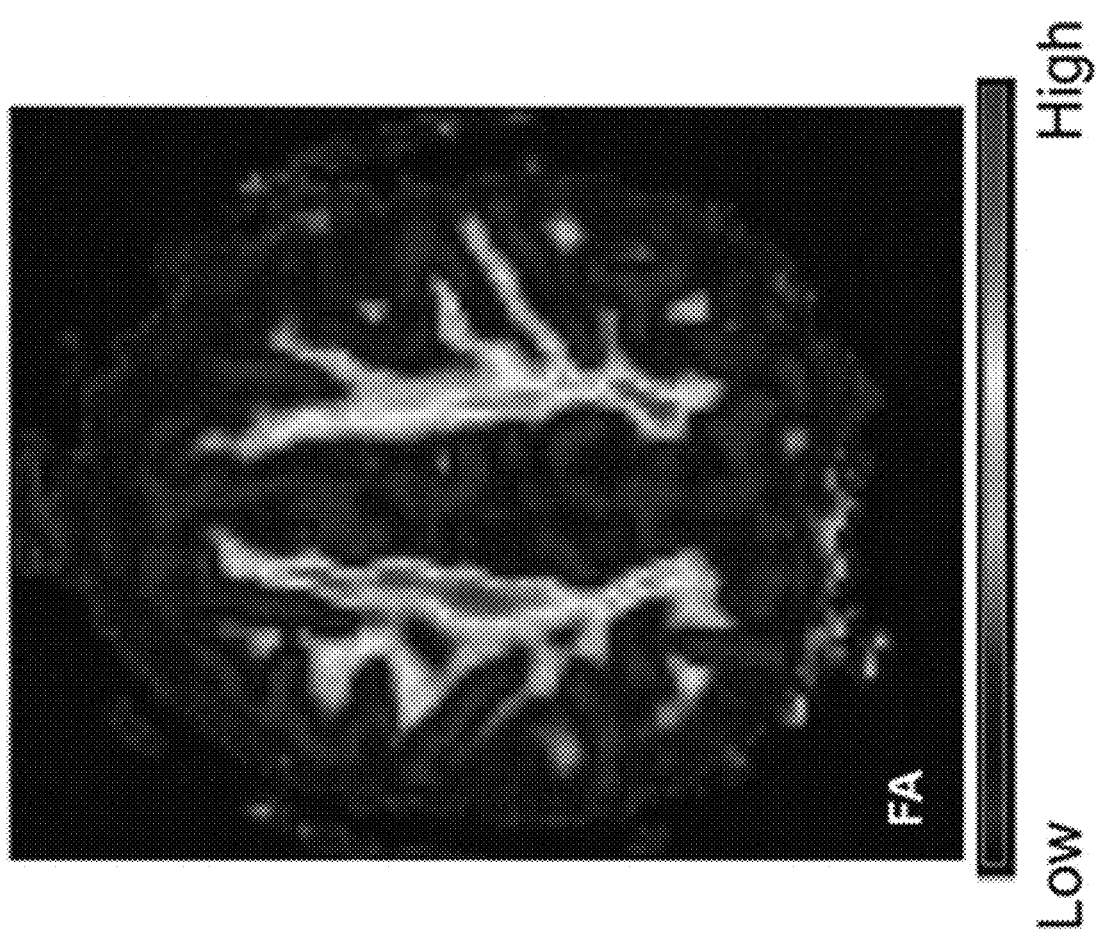
FIG. 14B is a picture showing the case of cerebral infarction in the left cerebral hemisphere with great function recovery. The picture indicates that the difference between the left and right in the FA in the precentral gyrus is small.

The ratio between FA of the precentral gyrus on the lesion side and that on the healthy side obtained from the diffusion image data prior to the cell administration (r=−0.89, p=0.04) showed a significant negative correlation with the change in mRS (FIG. 13). It is considered that the extent of the decrease in FA resulting from cerebral infarction reflects the function recovery. FIG. 13 indicates that FA of the precentral gyrus on the lesion side and the healthy side needs to be 0.84 or greater in order to obtain the change in mRS of 0.1 or greater. FIG. 14A and FIG. 14B show the difference in FA between left and right of the cases with a different function recovery extent.

The above results indicate that the ratio between the lesion side and the healthy side of DKI indexes prior to the cell administration shows a strong correlation with the function recovery extent.

Example 3: Evaluation of a State of a Motor Function with Indicators Other than BI and FMA According to DTI In this example, correlation with a motor function was evaluated using indicators (modified Rankin Scale (mRS), National Institute of Health Stroke Scale (NIHSS), and functional independence measure (FIM)) other than BI and FMA. The motor function was evaluated as of the case registration (after 14 days from cerebral infarction), 7 days before the cell cerebral administration (after 50 days in average from infarction), and after 1 year from the cell administration. Table 6 shows the result.

TABLE 6

| DTI FA value | | After 14 days from onset Precentral gyrus | 7 days before cell administration (2 months from onset) Precentral gyrus | After 1 year from administration Precentral gyrus |
|---|---|---|---|---|
| NIHSS | r | 0.056 | 0.077 | 0.447 |
| | p | 0.91 | 0.87 | 0.31 |
| mRS | r | 0.144 | 0.204 | 0.403 |
| | p | 0.92 | 0.66 | 0.37 |
| FIM | r | 0.500 | 0.354 | 0.734 |
| | p | 0.25 | 0.44 | 0.06 |
| BI | r | 0.613 | 0.476 | 0.79 |
| | p | 0.14 | 0.28 | 0.03 |

This result also indicates a correlation between the FA value of when ROI was placed only in the precentral gyrus and the motor function improvement (the FA value of the precentral gyrus ROI and the BI improvement degree after 14 days from the onset, the FA value of the precentral gyrus ROI and the FIM improvement degree/BI improvement degree after 1 year from the administration).

(Note)

As disclosed above, the present disclosure has been exemplified with preferred embodiments of the present disclosure, but it is understood that the scope of the present disclosure should be interpreted based solely on the scope of claims. It is also understood that any patent, any patent application, and any references cited herein should be incorporated herein by reference in the same manner as the contents are specifically described herein. The present application claims priority to Japanese Patent Application No. 2019-181051 filed to Japan Patent Office on Sep. 30, 2019, the content of which being incorporated by reference in the same manner as if the entirety thereof constitutes the content of the present application.

INDUSTRIAL APPLICABILITY

The present disclosure is useful in industries of therapy, diagnosis or the like of central nervous diseases. The present disclosure can be utilized in the fields of regeneration medical treatment, development of cell medicaments, or the like.

REFERENCE SIGNS LIST

1 MRI apparatus
10 Nuclear magnetic resonance imaging unit
20 Computer
21 Interface unit
22 Inputting unit
23 Storage unit
231 Echo data storage unit
232 Reconstructed image storage unit
233 DTI image storage unit
234 Reference information storage unit
24 Computing unit
241 Image generating unit
241a Image reconstructing unit
241b DTI image generating unit
242 Image analyzing unit
242a Region of interest setting unit
242b FA calculating unit
242c rFA calculating unit
242d Recovery prediction computing unit
25 Outputting unit
26 Controlling unit

The invention claimed is:

1. A method for evaluating a state of a motor function of a patient who has or is suspected of having a brain injury, the method comprising:
    obtaining a physiological indicator value with an outer surface region on the side of an injured hemisphere of a brain of the patient as a region of interest; and
    performing computation to calculate a value indicating the state of the motor function of the patient by comparing the physiological indicator value with a reference physiological indicator value, wherein the region of interest is set to a precentral gyrus of the brain.

2. The method of claim 1, wherein the physiological indicator value is obtained from a diffusion weighted image of the brain of the patient which is obtained by diffusion tensor imaging (DTI) method or diffusion kurtosis imaging (DKI) method.

3. The method of claim 1, wherein the physiological indicator value includes an FA (fractional anisotropy) value.

4. The method of claim 1, wherein the state of the motor function is a state of a motor function after regeneration therapy.

5. The method of claim 1, wherein the reference physiological indicator value is obtained with an outer surface region on the side of an uninjured hemisphere of the brain of the patient as a region of interest.

6. The method of claim 1, wherein the performing computation calculates a value represented by the physiological indicator value/the reference physiological indicator value.

7. The method of claim 1, wherein the performing computation evaluates the state of the motor function of the patient by substituting the calculated value indicating the state of the motor function of the patient in a regression line which is prepared in advance and has a value indicating a state of a motor function of a patient and a motor function recovery degree as variables.

8. The method of claim 1, wherein the performing computation calculates a level of a likelihood that the patient reaches a desired motor function recovery degree after regeneration therapy by comparing the calculated value indicating the state of the motor function of the patient with a reference value which is prepared in advance.

9. The method of claim 1, wherein the physiological indicator value is obtained from a diffusion weighted image of the brain of the patient which is obtained by diffusion tensor imaging (DTI) method or diffusion kurtosis imaging (DKI) method, and the physiological indicator value includes an FA (fractional anisotropy) value.

10. The method of claim 1, wherein the physiological indicator value is obtained from a diffusion weighted image of the brain of the patient which is obtained by diffusion tensor imaging (DTI) method or diffusion kurtosis imaging (DKI) method.

11. The method of claim 1, wherein the physiological indicator value includes an FA (fractional anisotropy) value.

12. The method of claim 1, wherein the physiological indicator value is obtained from a diffusion weighted image of the brain of the patient which is obtained by diffusion tensor imaging (DTI) method or diffusion kurtosis imaging (DKI) method, and the physiological indicator value includes an FA (fractional anisotropy) value.

13. A storage medium for storing a computer program for causing a computer to execute processing of a method for evaluating a state of a motor function of a brain of a patient who has or is suspected of having a brain injury, wherein the method comprises the following processes:
    causing the computer to obtain a physiological indicator value with an outer surface region on the side of an injured hemisphere of the brain of the patient as a region of interest; and
    causing the computer to perform computation to calculate a value indicating the state of the motor function of the patient by comparing the physiological indicator value with a reference physiological indicator value, wherein the region of interest is set to a precentral gyrus of the brain.

14. A system for evaluating a state of a motor function of a brain of a patient who has or is suspected of having a brain injury, the system comprising:

a means for storing a physiological indicator value with an outer surface region on the side of an injured hemisphere of the brain of the patient as a region of interest; and a means for performing computation to calculate a value indicating the state of the motor function of the patient by comparing the physiological indicator value with a reference physiological indicator value, wherein the region of interest is set to a precentral gyrus of the brain.

15. An image analysis apparatus comprising:

a region of interest setting unit that sets an outer surface region on the side of an injured hemisphere as a first region of interest and sets an outer surface region on the side of an uninjured hemisphere as a second region of interest in a diffusion weighted image of a brain of a patient who has or is suspected of having a brain injury;

a physiological indicator value calculating unit that calculates an injured hemisphere-side physiological indicator value and an uninjured hemisphere-side physiological indicator value in the first region of interest and the second region of interest, respectively; and a computing unit that performs computation to calculate a value indicating a state of a motor function of the patient by comparing the injured hemisphere-side physiological indicator value and the uninjured hemisphere-side physiological indicator value, wherein the region of interest is set to a precentral gyrus of the brain.

16. An MRI apparatus comprising:

a nuclear magnetic resonance imaging unit that images a brain of a patient who has or is suspected of having a brain injury;

an image generating unit that generates a diffusion weighted image from echo data that the nuclear magnetic resonance imaging unit acquires;

a region of interest setting unit that sets an outer surface region on the side of an injured hemisphere as a first region of interest and sets an outer surface region on the side of an uninjured hemisphere as a second region of interest in the diffusion weighted image;

a physiological indicator value calculating unit that calculates an injured hemisphere-side physiological indicator value and an uninjured hemisphere-side physiological indicator value in the first region of interest and the second region of interest, respectively; and a computing unit that performs computation to calculate a value indicating a state of a motor function of the patient by comparing the injured hemisphere-side physiological indicator value and the uninjured hemisphere-side physiological indicator value, wherein the region of interest is set to a precentral gyrus of the brain.

* * * * *